US011470870B2

(12) United States Patent
Van Mastrigt et al.

(10) Patent No.: US 11,470,870 B2
(45) Date of Patent: Oct. 18, 2022

(54) LIQUID FLAVOURING INGREDIENT PRODUCED BY FERMENTATION

(71) Applicants: Arla Foods amba, Viby J (DK); Wageningen Universiteit, PB Wageningen (NL)

(72) Inventors: Oscar Van Mastrigt, Wageningen (NL); Eilt Johannes Smid, Wageningen (NL); Tjakko Abee, Wageningen (NL); Søren K. Lillevang, Viby J (DK); Mette Nørtoft Kristensen, Viby J (DK)

(73) Assignees: Arla Foods amba, Viby J (DK); Wageningen Universiteit, PB Wageningen (NL)

( * ) Notice: Subject to any disclaimer, the term of this patent is extended or adjusted under 35 U.S.C. 154(b) by 0 days.

(21) Appl. No.: 17/265,492

(22) PCT Filed: Aug. 9, 2019

(86) PCT No.: PCT/EP2019/071498
§ 371 (c)(1),
(2) Date: Feb. 2, 2021

(87) PCT Pub. No.: WO2020/030811
PCT Pub. Date: Feb. 13, 2020

(65) Prior Publication Data
US 2021/0195932 A1 Jul. 1, 2021

(30) Foreign Application Priority Data
Aug. 10, 2018 (EP) .................................... 18188490

(51) Int. Cl.
A23L 27/24 (2016.01)
A23C 9/123 (2006.01)
(Continued)

(52) U.S. Cl.
CPC .............. A23L 27/25 (2016.08); A23C 9/123 (2013.01); A23C 9/127 (2013.01); A23C 9/1307 (2013.01); A23C 9/1322 (2013.01)

(58) Field of Classification Search
CPC ......... A23L 27/25; A23C 9/123; A23C 9/127; A23C 9/1307; A23C 9/1322
(Continued)

(56) References Cited

U.S. PATENT DOCUMENTS 4,001,437 A    1/1977 Jaeggi et al.
4,432,997 A *  2/1984 Reimerdes ........... A23C 19/063
                                                    426/7
(Continued)

FOREIGN PATENT DOCUMENTS

DK    0436/96     10/1997
EP    0058856 A1   9/1982
(Continued)

OTHER PUBLICATIONS

Wiltner, Kefir—the drink of the 120-year-olds, 2017, https://www.living-keto.de/kefir-das-getraenk-der-120-jaehrigen/ (Year: 2017).*
(Continued)

Primary Examiner — Brent T O'Hern
(74) Attorney, Agent, or Firm — Knobbe, Martens, Olson & Bear, LLP

(57) ABSTRACT

The present invention relates to a novel method of preparing a liquid flavouring ingredient by use of fermentation. In particular, the method involves recycling a part of the microorganisms used in the fermentation of flavour and aroma compounds back to the bioreactor for fermentation, while another part of the microorganisms are maintained in the obtained liquid flavouring ingredient. The obtained liquid flavouring ingredient is suitable for use as a taste enhancer and can be used in food products, such as dairy (Continued)

products, sauces, dressings, seasonings, meat products, bread, and sauerkraut.

12 Claims, 9 Drawing Sheets

(51) Int. Cl.
    *A23C 9/127*     (2006.01)
    *A23C 9/13*     (2006.01)

(58) Field of Classification Search
    USPC .......................................................... 426/534
    See application file for complete search history.

(56) References Cited

U.S. PATENT DOCUMENTS

| | | |
|---|---|---|
| 5,260,216 A | 11/1993 | Hirose et al. |
| 2005/0123646 A1 | 6/2005 | Crow et al. |
| 2008/0260905 A1 | 10/2008 | Gregory et al. |
| 2014/0024090 A1 | 1/2014 | Doig et al. |

FOREIGN PATENT DOCUMENTS

| | | |
|---|---|---|
| EP | 0191513 B1 | 1/1989 |
| EP | 1158042 A2 | 11/2001 |
| EP | 1469738 B1 | 10/2004 |
| EP | 1759588 A1 | 3/2007 |
| EP | 1915913 A1 | 4/2008 |
| WO | WO 91/16415 A1 | 10/1991 |
| WO | WO 03/047358 A1 | 6/2003 |
| WO | WO 2012/085011 A1 | 6/2012 |

OTHER PUBLICATIONS

Anonymous, "Kefir—Das Getrankder120-Jährigen" Jan. 2017, pp. 1-23, XP-002788675 https://www.living-keto.de/kefir-das-getraenk-der-120-jaehrigen.

Bollig, Brigitte et al., "Fast and Simple Determination of Free Amino Acids in Milk" Jun. 30, 2015, XP002788676, pp. 1-4; http://www.chromatographyonline.com/fast-and-simple-determination-free-amino-acids-mik.

International Search Report for PCT/EP2019/071498 dated Oct. 29, 2019.

\* cited by examiner

LIQUID FLAVOURING INGREDIENT PRODUCED BY FERMENTATION

CROSS REFERENCE TO RELATED APPLICATIONS

This application is a U.S. National Phase Application of PCT International Application Number PCT/EP2019/071498, filed on Aug. 9, 2019, designating the United States of America and published in the English language, which is an International Application of and claims the benefit of priority to European Patent Application No. 18188490.9, filed on Aug. 10, 2018. The disclosures of the above-referenced applications are hereby expressly incorporated by reference in their entireties.

TECHNICAL FIELD OF THE INVENTION

The present invention relates to a process for preparing a liquid flavouring ingredient and said liquid flavouring ingredient. In particular, the present invention relates to preparing a liquid flavouring ingredient by use of fermentation where the liquid flavouring ingredient is produced by microorganisms cultivated at near-zero growth rates while having an increased taste and aroma, preferably an intense taste of cheese.

BACKGROUND OF THE INVENTION

The cheese ripening process consists of a variety of enzymatic activities that lead to the degradation of macromolecules into small breakdown products. One of the most important activities is the breakdown of proteins by means of rennet, bacterial enzymes and plasmin, which causes successively development of texture, taste, and aroma compared to a young (aged less than 24 hours) cheese. The proteins are broken down during the ripening period and the older the cheese is, the more breakdown happens. After having broken the proteins down to amino acids, flavour compounds are formed by bacterial enzymes and the older the cheeses are, the more cheese flavour is developed. This process requires long ripening times in the range of weeks to months. However, this long ripening time have disadvantages since much storage place is required. In addition, capital is bound in the ripening cheeses.

Hence, a process of preparing a flavour ingredient which resembles the taste and aroma of a long time ripened cheese would be advantageous, such as a flavour ingredient that could be added to a short time (24 hour) ripened cheese and have the taste of a full ripened cheese (i.e. ripened for 6 months).

SUMMARY OF THE INVENTION

Thus, an object of the present invention relates to providing an improved method of preparing a liquid flavouring ingredient which can be used as a taste enhancer in various food products.

In particular, it is an object of the present invention to provide an improved method of preparing a liquid cheese flavouring ingredient to be used in the manufacture of cheese to avoid ripening, but which has a flavour as a full ripened cheese.

Thus, one aspect of the invention relates to a process for preparing a liquid flavouring ingredient, comprising the steps:

i) providing a feed material to be fermented, wherein said feed material comprises hydrolysed proteins and/or a mixture of free amino acids in a liquid solution in an amount of at least 0.1% w/v;

ii) providing one or more microorganisms and inoculate the feed material of step i) with the one or more microorganisms in a bioreactor and fermenting under conditions for growth to prepare a flavoured liquid with microorganisms;

iii) removing flavoured liquid with microorganisms from the bioreactor;

iv) recycle a part of the microorganisms removed from the bioreactor in step iii) back to the bioreactor; and maintain a part of the microorganisms removed from the bioreactor in step iii) in the flavoured liquid to obtain a liquid flavouring ingredient.

Another aspect of the present invention is to provide a liquid flavouring ingredient obtainable by the process according to the invention.

Yet another aspect of the present invention is the use of the liquid flavouring ingredient obtainable by the process according to the invention in a food product.

Still another aspect of the present invention is the use of the liquid flavouring ingredient obtainable by the process according to the invention as a taste enhancer.

BRIEF DESCRIPTION OF THE FIGURES

FIG. 2 shows pictures of bacterial cells.

Figure 1A:
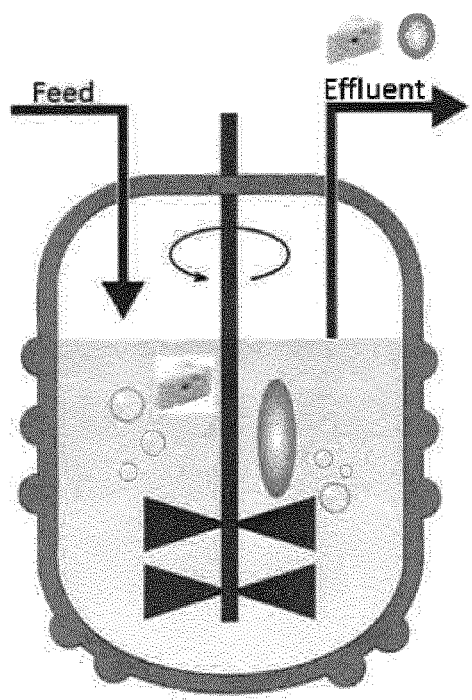
FIG. 1A shows a traditional fermentation process (bioreactor) with no recirculation of microorganisms.

The present invention will now be described in more detail in the following.

DETAILED DESCRIPTION OF THE INVENTION

Definitions:

Prior to discussing the present invention in further details, the following terms and conventions will first be defined:

Liquid Flavouring Ingredient:

The term liquid flavouring agent refers to a flavouring agent in a liquid or fluid state. The term "liquid" and "fluid" may be used interchangeably.

The term "liquid" or "fluid" means in the context of the present invention a product having a moisture content of 20 vol-% or more, in particular 25 vol-% or more.

The term "flavour" refers to the combined effect of taste and smell (odour), while the term "aroma" refers to odour/smell only.

Feed Material:

The term "feed material" is according to the present invention to be understood in its broadest sense. The "feed material" comprises hydrolysed proteins and/or a mixture of free amino acids in a liquid solution such that said hydrolysed proteins and/or amino acids can be converted to aromatic compounds during fermentation with microorganisms. In addition, the feed material may comprise one or more sugars, such as monosaccharides or disaccharides. The microorganisms consume the sugar and therefore the one or more sugars are used for growth of the microorganisms.

In an embodiment of the present invention, the feed material comprises one or more disaccharide, preferably lactose. Therefore, the feed material may in an embodiment comprise a) hydrolysed proteins and or a mixture of free amino acids, and b) lactose.

In some embodiments of the invention, the feed material comprises one or more monosaccharide, such as glucose and galactose.

In another embodiment of the invention, the feed material is a dairy product, said dairy product has been subjected to protein hydrolysis and therefore comprises hydrolysed proteins and lactose.

In an embodiment, the feed material is furthermore subjected to hydrolysis of lactose. Hereby, lactose in the feed material is converted to glucose and galactose. Hence, the obtained glucose and galactose is used as substrate for the microorganisms. The advantage of converting lactose to glucose and galactose and use glucose and galactose as a substrate instead of lactose is that microorganisms that are not able to ferment lactose, but can ferment glucose or galactose, can be used.

In order for the feed material to be suitable for the fermentation according to the invention, the feed material is a liquid solution. By the term "liquid solution" is in the context of the present invention meant a solution in a liquid state. The solid content of the liquid may vary and the liquid may for example have a higher solid content than original bovine milk. However, the feed material is not in the form of a powder or granulate when used for fermentation. The feed material may however be a powder reconstituted in water. It is important that the feed material is in a liquid state since the fermentation process needs liquid for the microorganisms to grow. In the context of the present invention, the liquid solution of the feed material will have a moisture content of 20 vol-% or more, in particular 25 vol-% or more. In one embodiment of the invention, a sufficient water content of the feed material (i.e. a water content of 20 vol-% or more) is provided by mixing a product with an insufficient water content (i.e. a water content of below 20-vol-%), with a product with a sufficient water content. Hereby, a feed material with an appropriate water content of the mixture is provided.

Hence, in a further embodiment, the inoculation of the feed material with microorganisms is supplemented with addition of water or a water-based fluid and thus provides a mixture with appropriate water content for fermentation to take place in step ii).

The water and water-based fluid which may be added to the feed material can optionally be treated before addition to the feed material. Said water may for example be treated by addition of chemical compounds and/or chemical compositions, such as salts, minerals, vitamins, buffering substances, organic or inorganic acids and the like. The treated water including chemical compounds and/or chemical compositions may improve the fermentation process.

The feed material comprises in an ascpect of the invention hydrolysed proteins and/or free amino acids in an amount of at least 0.1% w/v.

In the context of the present invention, the term "hydrolysed proteins" means a composition comprising proteins that has been subjected to protein hydrolysis. By protein hydrolysis, the protein is cleaved into peptides and free amino acids, and therefore, the "hydrolysed proteins" comprises peptides and/or free amino acids. The term "hydrolysed proteins" also includes a mixture of intact protein and a proteolytic microorganisms. When the feed material comprises intact protein, the proteolytic microorganisms hydrolyse the intact protein to peptides and free amino acids during fermentation. In an embodiment of the present invention, the hydrolysed protein should have been hydrolysed to a level including peptides having a length of 5 amino acids or less and/or free amino acids. Preferably, the hydrolysed protein comprises peptides having a length of 3 amino acids or less. Small peptides can be taken up by the cell of the microorganism (for example bacteria) and intracellular be degraded to release free amino acids in the cytoplasm of the microorganism. Many microorganisms, for example lactic acid bacteria, contain multiple peptide transporters and peptidases to take up small peptides and degrade them to amino acids.

In another embodiment, the hydrolysed protein is hydrolysed to an amino acid level. By the term "hydrolysis to amino acid level" is meant that at least 80% of the amino acids bound in the protein is hydrolysed to free amino acids, such as at least 85% of the amino acids bound in the protein is hydrolysed to free amino acids, preferably at least 90% of the amino acids bound in the protein is hydrolysed to free amino acids, even more preferably at least 95% of the amino acids bound in the protein is hydrolysed to free amino acids.

Proteins have to be hydrolysed to free amino acids and/or small peptides having a length of 5 amino acids or less, since the microorganisms convert amino acids and small peptides to flavour compounds during the fermentation step. Flavour components is not formed from intact proteins.

The feed material may in a further embodiment of the invention comprise free amino acids and a low amount of peptides. For example, the amount of amino acids bound in peptides is 10% by weight or less based on the total amino acid content, such a 8% by weight or less, preferably 5% by weight or less based on the total amino acid content.

The feed material to be fermented comprises hydrolysed proteins and/or a mixture of free amino acids in a liquid solution. In a preferred embodiment of the invention, the hydrolysed proteins and/or mixture of free amino acids have a dairy origen.

In the context of the present invention, the term "dairy" refers to hydrolysed dairy proteins, such as peptides and/or amino acids obtained from dairy proteins. Proteins normally occurring in dairy products are casein and whey proteins, where α-lactalbumin and β-lactoglobulin are the major whey proteins in bovine milk. Dairy proteins may also comprise casein-glycomacropeptide (cGMP) derived from whey in cheese production.

In a further embodiment of the invention, the feed material may be a liquid dairy material that has been subjected to protein hydrolysis. Said protein hydrolysed liquid dairy material will comprise hydrolysed proteins and/or amino acids which can be fermented to flavour compounds in the method according to the present invention. In addition, using a liquid dairy material as a feed material in the present invention, the feed material comprises lactose which can be used as substrate for the microorganisms driving the fermentation process.

In an embodiment of the invention, the feed material is a hydrolysed dairy product obtained from hydrolysing a liquid dairy product such as whole milk, low-fat milk, reduced fat milk, semi-skimmed milk, skim milk, butter milk, reconstituted milk powder, heat treated milk (e.g. pasteurized milk, sterilized milk, condensed milk, evaporated milk and UHT milk), raw unfiltered milk, de-caseinated milk, micellar casein isolate (MCI), and homogenized milk. Whey may also be used as feed material, but another flavour is obtained with whey than with milk.

Furthermore, the liquid dairy product used as feed material in the process according to the present invention may be based on milk from mammals such as cows, buffalos, goats, sheep, yaks, pigs, camels, horses, ewes, mares or mixtures thereof. In a preferred embodiment of the present invention, the feed material is protein hydrolysed milk from cows, i.e. bovine milk.

In another embodiment of the present invention, the feed material as such is not a dairy product, but the feed material is an artificial substrate, such as a liquid solution comprising hydrolysed proteins and/or amino acids to be used in flavour development and one or more sugars used for growth of the microorganisms. The hydrolysed proteins and/or free amino acids may however be from a dairy origin. The sugar may for example be one or more of monosaccharides and disaccharides, i.e. one or more selected from the group of glucose, galactose and lactose.

Thus, the feed material used in the process according to the present invention is a liquid solution and said liquid solution may be selected from one or more of the following: a liquid dairy product (such as milk or whey), water, peptone water, saline water, plant derived liquid substances. The plant derived liquid substances may for example be based on beans from legumes such as soy (*Glycine max*), lupine (*Lupinus albus*) and other members of the family of Fabaceae.

In an embodiment of the invention, the feed material is an artificial made feed material comprising water (any type), a mixture of peptides having a length of 5 amino acids or below and/or free amino acids and one or more sugars.

Therefore, the "feed material" of the present invention comprises in an embodiment a) hydrolysed protein and/or free amino acids and b) one or more sugars. The hydrolysed protein (or peptides) or free amino acids is used for flavour development, while the sugar is used for growth of microorganisms. Citrate also serves as substrate in the production of aroma compounds. For example, citrate is used in the formation of acetoin and diacetyl, i.e. for providing a buttery aroma.

In an aspect of the present invention, the feed material comprises hydrolysed protein and/or free amino acids in an amount of at least 0.1% weight/volume (w/v). This is to be understood as the total amount of amino acids in the feed material, i.e. both the amino acids bound in peptides and free amino acids. The feed material may for example comprise hydrolysed protein and/or free amino acids in an amount of at least 0.3% w/v, such as at least 0.5% w/v, for example at least 0.7% w/v, preferably at least 1% w/v, and more preferably at least 2% w/v of total amino acids in the feed material. In a further embodiment, the feed material is hydrolysed micellar casein isolate comprising hydrolysed protein and/or free amino acids in an amount of at least 5% w/v.

In the context of the present invention, the term "w/v" as in amount hydrolysed protein and/or free amino acids in the feed material means: the weight percentage of hydrolysed protein and/or free amino acids per volume of feed material. For example 1% w/v of hydrolysed protein and/or free amino acids in a feed material means 1 g hydrolysed protein and/or free amino acids per 100 ml feed material, or 10 g hydrolysed protein and/or free amino acids per 1 litre feed material.

In a further embodiment of the invention, the feed material comprises a total amount of hydrolysed protein and/or free amino acids in the range of 0.1% to 15% w/v, such as 0.5% to 13% w/v of hydrolysed protein and/or free amino acids in the feed material, preferably 1% to 12% w/v of hydrolysed protein and/or free amino acids in the feed material, even more preferably 2% to 10% w/v of total amino acids in the feed material.

The feed material may comprise one or more sugars, and said one or more sugars may for example be selected from the group of lactose, glucose and galactose. In a preferred embodiment of the invention, the sugar is lactose.

In a further embodiment of the invention, the feed material comprises a) hydrolysed proteins and/or free amino acids and b) one or more sugars, wherein the ratio between a) and b) is at least 1:2 by weight (w/w), preferably at least 1:1 by weight, and even more preferably at least 2:1 by weight.

Figure 2A:
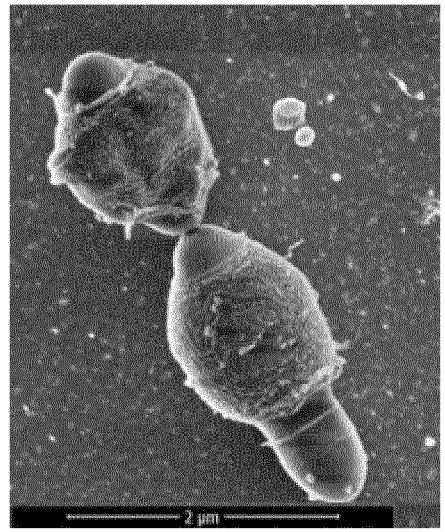
FIGS. 2A and 2B show microbial cells from the fermentation process according to the present invention where microorganisms are recycled to the bioreactor and the microorganisms therefore have been subjected to starving.
Figure 2B:
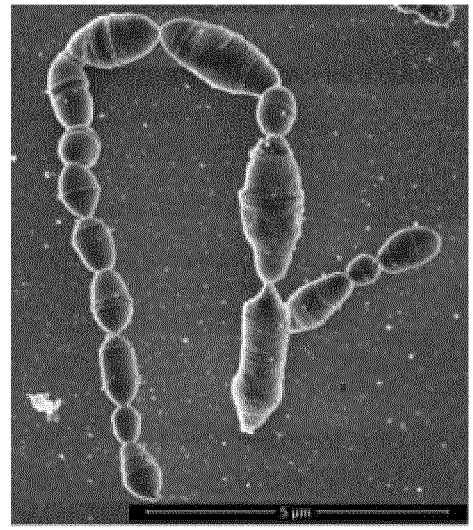
Figure 2C:
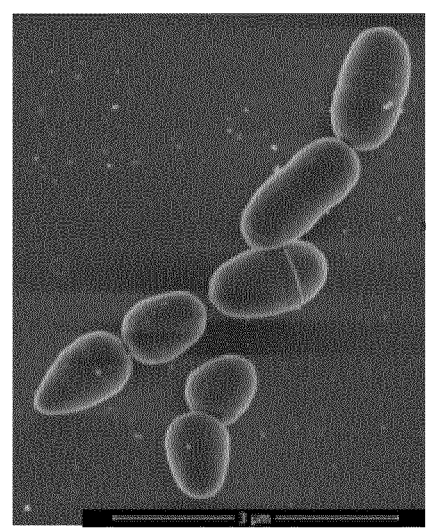
FIG. 2C shows a microbial cell from a fermentation process where no microorganisms are recycled.

The sugar provides feed for the microorganisms and hence growth of the microorganisms while, the microorganisms convert the hydrolysed proteins and/or free amino acids to flavour compounds under the fermentation step ii) in the process according to the invention. It is however important to keep the sugar content low, and the sugar content should preferably be less than the content of hydrolysed proteins and/or free amino acids. When the sugar content is low, the microorganisms will be in need of feed and when the microorganisms are starving, they will consume other compounds. When the microorganisms have sufficient sugar, flavour components are not formed. Instead lactic acid is produced. Lactic acid will result in decreased pH and a decreased pH will inhibit the growth of microorganisms. Therefore, when the sugar content is low, the conversion of hydrolysed protein and free amino acids to flavour compounds by the microorganisms are increased. In addition, when the microorganisms are starving, they become larger but also change their shape from cocoid to rod-shaped. The microorganisms are therefore fed with a low amount of sugar, i.e. an amount merely sufficient for the microorganisms to survive. FIG. 2 shows the difference in size between microorganisms (bacteria) which are starving versus microorganisms which are not starving. FIGS. 2A and 2B shows microorganisms used in the process according to the present invention and therefore are starving, since the amount of sugar in the feed material is kept low. FIG. 2C shows a bacterium used in a traditional fermenting process where liquid with flavour components and bacteria are removed from the bioreactor with no recirculation of the bacterial biomass. It is clearly shown in the figures that the bacteria in the environment according to the present invention become bigger in size than the bacteria in a traditional fermentation process.

In an embodiment of the present invention, the feed material comprises a) hydrolysed proteins and/or free amino acids and b) one or more sugars, wherein the ratio between a) and b) is in the range of from 1:2 to 15:1 by weight. Preferably, the feed material comprises a) hydrolysed proteins and/or free amino acids and b) one or more sugars, wherein the ratio between a) and b) is in the range of from 2:3 to 12:1 by weight, even more preferably in the range of from 1:1 to 10:1 by weight.

In an embodiment of the invention, the feed material comprises sugars in the range of from 0.1% to 2.0% w/v. Preferably, the feed material comprises sugars in the range of from 0.2% to 1.5% w/v, even more preferably from 0.25% to 1.0% w/v.

In a further embodiment of the process according to the present invention, alpha-keto acids are added to the bioreactor in step ii). Alpha-keto acids are added to boost and increase the flavour development and speed up the flavour development.

In still a further embodiment of the invention, one or more selected from the group of fats, lipids and fatty acids is added to the bioreactor. The fats, lipids and fatty acids may for example be present in the feed material used for fermentation. Furthermore, the fats, lipids and fatty acids may in a preferred embodiment be of dairy origin. Many cheese aroma compounds, such as methyl ketones originate from fat and fatty acids and addition of fats and/or fatty acids may therefore increase the formation of certain aroma coumpounds.

In an even further embodiment of the invention, the feed material further comprises one or more selected from the group of intact protein, polysaccharides, fats, fatty acids, organic acids, and alcohols.

In also an embodiment of the invention, the feed material further comprises one or more selected from the groups of vitamins, nucleotides, and metals. The nucleotides may for example be one or more of adenine, uracil, xanthine and guanine.

The feed material used in the process according to the present invention may in an embodiment be filtered over a microfiltration cross-flow membrane before added to the bioreactor in order to remove larger particles, such as contaminants.

Fermentation:

The fermentation according to the present invention is a new cultivation method with slow growth of microorganisms, such that an efficient flavour production is formed. In the present invention of preparing a liquid flavouring ingredient, a feed material is inoculated with one or more microorganisms and during fermentation flavour components is obtained.

In a traditional fermentation system a feed or substrate is added to the bioreactor, and after fermentation a liquid with flavour compounds and microorganisms is removed. This traditional fermentation system which is shown in FIG. 1A has a drawback because liquid with flavour compounds and microorganisms are continuously or batch wise removed from the bioreactor which results in a decreased amount of microorganisms in the bioreactor when liquid (effluent) is removed from the bioreactor. Hence, microorganisms need to grow continuously.

Figure 1B:
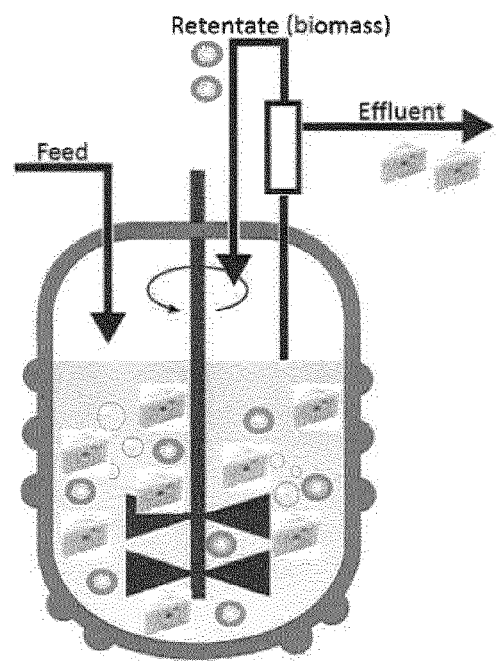
FIG. 1B shows a fermentation process where all microoganisms are recycled to the bioreactor.

This traditional fermentation system can however be more advanced by filtering the removed fermented liquid and recycle the microorganisms to the bioreactor, see FIG. 1B. This way the amount of microorganisms in the bioreactor are maintained high, i.e. at a level of $10^{10}$ or $10^{11}$ cells/ml.

Figure 1C:
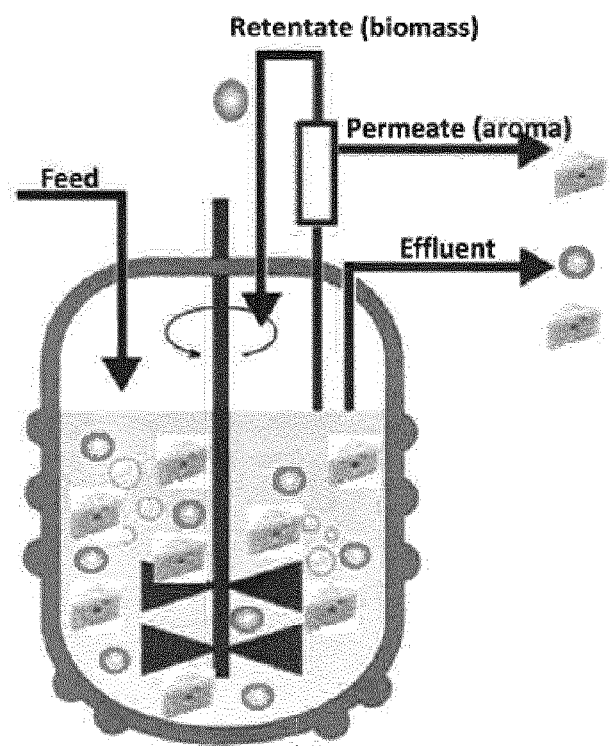
FIG. 1C shows a fermentation process (bioreactor) according to the present invention where a part of the microorganisms are recycled back to the bioreactor.

The inventors of the present invention have now found out that by recycling only a part of the microorganisms back to the bioreactor, the amount of the microorganisms in the bioreactor can be maintained high, around $10^{10}$ cells/ml, while obtaining an increased aromatic flavour in the liquid obtained from fermentation which comprises flavour compounds and some microorganisms. This new process of preparing a liquid flavour ingredient is shown in FIG. 1C. It has surprisingly been shown by the inventors of the present invention that by recycling a part of the microbial biomass in the fermented liquid back to the bioreactor while maintaining some microorganisms in the fermented liquid results in an increased production of flavour and aroma compounds.

Thus, the present invention relates to utilization of amino acids from any protein source in a bioreactor to produce flavour compounds, where the fermentation process involves recycling a part of the microorganisms from the fermented liquid with flavour compounds back to the biorector, and maintain another part of the microorganisms in the fermented liquid with flavour compounds. The liquid flavour ingredient obtained by the method according to the present invention will provide a concentrated flavour which can be added to any cheese or other food products giving a unique flavour.

With the process according to the present invention, a filtration device makes it possible to lead liquid (effluent) with flavour compounds out of the filter and lead living microorganisms back into the bioreactor. In this way, the concentration of microorganisms in the bioreactor will be very high and the flavour formation activity will therefore be high too. Furthermore, by maintaining a part of the microorganisms in the obtained liquid flavour ingredient, a flavour with a strong intensity is obtained as compared to recycle all the microorganisms back to the bioreactor. If all microorganisms are recycled to the bioreactor, the flavour will be less intensive. The inventors of the present invention have surprisingly found out that by recycling a part of the microorganisms back to the bioreactor, the amount of the microorganisms in the bioreactor can be as high as $10^9$ to $10^{10}$ cells per ml and at a near zero growth rate, while having another part of the microorganisms, both alive and dead, maintained in the fermented liquid flavour provides a unique flavour. The present inventors have surprisingly found out that a part of the flavour components is attached to the cell membrane of these microorganisms being dead and alive. Therefore, a liquid flavour ingredient prepared by the process according to the present invention will provide a very intense flavour.

In FIGS. 1A-1C, the term biomass refers to microorganisms, including bacteria. The term "biomass" covers the terms "bacteria" and "microorganisms" Microorganisms cover bacteria and fungi. The fungi may for example be yeast.

In the traditional fermentation process (shown in FIG. 1A), the growth rate of microorganisms can be controlled. However, the growth rate will be limited to 0.05 $h^{-1}$ or higher. The term "$h^{-1}$" refers to reciprocal hour. In the context of the present invention, growth rate means balanced growth rate where $dN/dt=\mu N$. N is the concentration of microorganisms, t is the time and $\mu$ is the growth rate. The amount of microorganisms in the bioreactor will be low, because fermented liquid continuously will be removed from the bioreactor, and as a result thereof, the flavour development will also be low.

In the fermentation process (as shown in FIG. 1B) where biomass is recycled from the fermented liquid back to the bioreactor, the growth rate of biomass is very low and close to zero. This is hereinafter called near zero growth. Since the microorganisms (biomass) are recycled to the bioreactor, it is possible to obtain a high biomass concentration in the bioreactor and thus obtain a high productivity of flavour compounds. However, it is not possible to control the growth rate of the microorganisms with this fermentation system and the filters may be clogged due to accumulation of unwanted particles and dead bacterial cells. Furthermore, it is not possible to harvest the flavour compounds that are attached to the cell membrane and which result in an intense flavour.

However, the inventors of the present invention have surprisingly shown that by recycling only a part of the biomass (microorganisms) back to the bioreactor (FIG. 1C) and having a low amount of sugar, a near-zero growth rate of the biomass can still be obtained, while having some biomass in the fermented flavour liquid. Furthermore, with the fermentation system according to the present invention, it is possible to control the growth rate of the biomass resulting in high reproducibility. On the contrary, the fermentation system with complete recirculation (FIG. 1B) of the biomass to the bioreactor has a low reproducibility. Without being bound by any theory, the inventors of the present invention have shown that by having a fermentation process running at near zero growth rate, a fermented liquid with some biomass therein will have a more intense flavour. It is believed that some flavour compounds adhere to the microbial cell and therefore a more increased flavour is obtained where the fermented liquid flavour comprises microorganisms.

In the process according to the present invention, there will be a small growth of the microorganisms (0.05 $h^{-1}$ or lower), since the amount of sugar is low and microorganisms are recycled to the bioreactor. Hereby, many microorganisms are competing for the feed, and the growth of microorganisms will as a result thereof be low. In addition, a fraction of the microorganisms are continuously removed with the flavoured liquid. Therefore, the growth rate of microorganisms in the bioreactor is so low that it is considered a near-zero growth.

In the context of the present invention, the process according to the invention is called a dual-efflux fermentation process. The dual-efflux fermentation process according to the present invention involves a bioreactor that may comprise one or more outlets for flavoured liquid with microorganisms. Therefore, removing flavoured liquid with microorganisms from the bioreactor according to step iii) in the process according to the first aspect of the present invention is by use of one or more outlets.

In one embodiment of the invention, removing flavoured liquid with microorganisms from the bioreactor is from two outlets, a) one outlet for removal of a first flavoured liquid with microorganisms followed by separation of the microorganisms from said flavoured liquid, and wherein said microorganisms are recycled to the bioreactor; and b) a second outlet for removal of a second flavoured liquid with microorganisms, and wherein c) said first flavoured liquid without microorganisms and said second flavoured liquid with microorganisms are mixed to obtain a liquid flavouring ingredient.

However, the dual-efflux fermentation process according to the present invention may also involve a bioreactor having only one outlet for fermented flavoured liquid with microorganisms, but where said flavoured liquid with microorganisms is subjected to a separation step to separate a part of the microorganisms from the fermented flavoured liquid. Therefore, in a further embodiment of the invention, removing flavoured liquid of step iii) is from one outlet, the microorganisms are separated from the flavoured liquid and a part of the microorganisms are recycled to the bioreactor and another part of the microorganisms are added to the flavoured liquid to obtain a liquid flavouring ingredient.

In the dual-efflux fermentation process according to the present invention, a high concentration of microorganisms (biomass) in the bioreactor is obtained, which results in a high productivity. In addition, the dual-efflux fermentation process provides less accumulation of unwanted particles and dead cells in the filter. The unwanted particles and dead cells may be washed out and therefore this system provides less clogging of the filter.

In a further embodiment of the invention, the feed material (and possible further components for the fermentation) is added to the bioreactor through one or more inlets. In an embodiment, the feed material is added thrugh one inlet, but in another embodiment, the feed material is added through two or more inlets. Addition of feed material by the use of two or more inlets is particularly preferred whed compounds are added to boost the aroma and flavour production, such as further addition of for example alpha-keto acids.

The process for preparing the liquid flavouring ingredient according to the present invention is a continuous process. By the term "continuous process" is meant continuous adding feed material and continuous removing obtained flavoured liquid.

With a process according to the present invention, where a part of the microorganisms present in the obtained flavoured liquid is recycled back to the bioreactor, it is possible to maintain the microbial cell count in the bioractor at a high level, such as at a level of $10^9$ to $10^{10}$ cells/ml. Thus, the concentration of microorganisms in the bioreactor according to the present invention is maintained in the range of $10^9$ to $10^{10}$ cells/ml.

Furthermore, in the process for preparing the liquid flavouring ingredient according to the present invention, i.e. with use of the dual-efflux fermentation system, the growth of microorganisms will have a very low growth rate, i.e. a "near-zero" growth rate. In an embodiment of the invention, the growth rate of biomass (microorganisms) is as low as 0.001 $h^{-1}$.

In an embodiment of the invention, the growth rate of biomass, i.e. microorganisms, in the bioreactor is from 0.001 to 0.1 $h^{-1}$. The growth rate of the microorganisms may in a preferred embodiment be from 0.0015 to 0.05 h$^{-1}$, such as from 0.0020 to 0.04 h$^{-1}$, most preferably from 0.0025 to 0.025 h$^{-1}$.

In another embodiment, the flow of media through the bioreactor, also called flow rate or dilution rate, is in the range of 0.001 to 0.5 h$^{-1}$. The optimal flow rate may vary dependent on the fermentation system used and the pumps used. However, any type of fermentation system may be used in the present invention, and the invention should therefore not be limited to the system or pump used. In a further embodiment, the flow rate is in the range of from 0.003 to 0.4 h$^{-1}$, such as from 0.0035 to 0.3 h$^{-1}$. In also an embodiment, the flow rate is in the range of from 0.001 to 0.05 h$^{-1}$, such as from 0.002 to 0.03 h$^{-1}$. In another embodiment, the flow rate is in the range of from 0.02 to 0.5 h$^{-1}$, such as in the range of 0.02 to 0.2 h$^{-1}$. The dilution rate is defined as the flow of the feed material divided by the volume of the liquid in the bioreactor. Thus, with a flow of the feed material of 0.1 L/h and a liquid volume in the fermentor of 1 L, the dilution rate is 0.1 h$^{-1}$. The total of all flow of liquids removed from the bioreactor sould be equal to the flow of the feed material to have a constant volume of liquid in the bioreactor.

As earlier described, a part of the microorganisms is separated from the obtained flavoured liquid after fermentation and is recycled back to the bioreactor. In an embodiment of the invention, the separation of microorganisms from flavoured liquid is by use of filtration, sedimentation and/or centrifugation. Filtration may for example be by use of microfiltration and the membrane used for microfiltration preferably has a pore size of 0.1 to 2.0 micrometer. In a preferred embodiment of the invention, the microorganisms are separated from flavoured liquid by use of cross-flow microfiltration. The use of cross-flow microfiltration avoids clogging of the filter. Preferably, the microorganisms are separated by use of filtration.

When using a milk based hydrolysate as feed material, there may be larger particles or contaminants present and therefore a higher risk of clogging the filters. Therefore, in an embodiment of the invention, the feed material is filtered before inoculating with microorganisms in step ii). The feed material may for example be filtered with a 0.2 micrometer cross-flow membrane.

In the context of the present invention, the term "a part" means that a substantial amount of the microorganisms present in the flavoured liquid removed from the bioreactor are separated from the flavoured liquid. However, not all microorganisms are removed from the flavoured liquid and recycled. In an embodiment of the invention, at least 20% by weight of the microorganisms are separated from the flavoured liquid and recycled to the bioreactor. In another embodiment, 20 to 95% by weight of the microorganisms in the flavoured liquid are recycled to the bioreactor. In the process according to the present invention, it is necessary with recirculation of microorganisms back to the bioreactor in order to obtain a near zero growth. In addition, it is important to maintain a part of the microorganisms in the obtained flavoured liquid to obtain an increased flavour development in the flavoured liquid. Preferably, 30 to 90% by weight of the microorganisms in the flavoured liquid are recycled to the bioreactor, even more preferably 40 to 85% by weight of the microorganisms from the flavoured liquid are recycled to the bioreactor, most preferably 50 to 80% by weight of the microorganisms from the flavoured liquid are recycled to the bioreactor.

If flavoured liquid with microorganisms is removed from two outlets, i.e. removal of a first flavoured liquid with microorganisms from one outlet and removal of a a second flavoured liquid with microorganisms from a second outlet, where the microorganisms in the first flavoured liquid are separated and recycled to the bioreactor, the first flavoured liquid and the second flavoured liquid with microroganisms are mixed in a ratio such that the amount of microorganisms in the obtained liquid flavouring ingredient is in the range of 5-80% as compared to the total amount of microorganisms removed from the bioreactor before recycling microorganisms.

In an embodiment of the invention, the amount of microorganisms in the obtained flavoured liquid is $10^8$ to $10^{10}$ cells/ml.

Microorganisms:

In the present invention one or more microorganisms are provided and added to the bioreactor to inoculate the feed material, and fermentation is conducted under conditions for growth to prepare a flavoured liquid with microorganisms. The microorganisms may be from one or more of bacterial species and fungi. The bacteria are preferably selected from Gram-positive bacteria and more preferably the bacteria are one or more selected from the group of lactic acid bacteria, acetic acid bacteria, bifidobacteria and propionibacteria. The fungi is preferably yeast.

The lactic acid bacteria may be one or more selected from the group of the following genera: *Carnobacterium, Enterococcus, Lactococcus, Lactobacillus, Streptococcus, Weisella, Leuconostoc, Oenococcus, Pediococcus, Vagococcus* and *Tetragenococcus.*

The propionibacteria includes species of the genus *Propionibacterium* and *Acidipropionibacterium.*

Examples of *Lactobacillus* species that may be used for fermentation in the present invention is *Lactobacillus plantarum, Lactobacillus casei, Lactobacillus paracasei* (preferably *Lactobacillus paracasei* subsp. *paracasei* F-19), *Lactobacillus rhamnosus, Lactobacillus reuteri, Lactobacillus delbrueckii,* (preferably *Lactobacillus delbrueckii* subsp. *bulgaricus*), *Lactobacillus helveticus* and *Lactobacillus fermentum*. Other species of the genus *Lactobacillus* may also be used. The strains can be used alone or in combination.

An example of a *Streptococcus* species that can be used in the fermentation according to the present invention is *Streptococcus thermophilus,*

The one or more microorganisms used in the present invention may also be a *Lactococcus*. An example of a *Lactococcus* species is *Lactococcus lactis*, preferably *Lactococcus lactis* subsp. *lactis, Lactococcus lactis* subsp. *cremoris*, and *Lactococcus lactis* subspecies *lactis* biovar *diacetylactis.*

In a preferred embodiment, the bacterial species is *Lactococcus lactis.*

In a preferred embodiment of the invention, the bacterial species is *Lactococcus lactis* subspecies *lactis* biovar *diacetylactis.*

Examples of *Bifidobacterium* species that can be used in the fermentation in the present invention include *Bifidobacterium anima/is,* preferably subsp. *lactis, Bifidobacterium breve, Bifidobacterium adolescentis, Bifidobacterium bifidum,* and *Bifidobacterium longum.*

Examples of *Leuconostoc* strains that can be used in the fermentation in the present invention includes *Leuconostoc mesenteroides*, preferably *Leuconostoc mesenteroides* subsp. *cremoris, Leuconostoc lactis, Leuconostoc pseudomesenteroides.*

In an embodiment of the invention, the acetic acid bacteria is one or more selected from the group of the genus *Gluconobacter*, the genus *Acetobacter* and the genus *Gluconacetobacter*.

Examples of *Gluconobacter* strains used in the present invention include *Gluconobacter oxydans*.

Examples of *Acetobacter* strains used in the present invention include *Acetobacter pasteurianus*.

In an embodiment of the invention, the one or more microorganisms include yeast. Yeast may be one or more selected from the group of the genus *Candida*, the genus *Pichia*, the genus *Saccharomyces*, the genus *Kiuveromyces*, the genus *Torulaspora* and the genus *Wickerhamomyces*.

Preferably, the yeast is a strain selected from the group of *Pichia kiuveri, Saccharomyces cerevisiae, Saccharomyces italicus, Candida kefyr, Kluyveromyces marxianus*, and *Kluyveromyces lactis*. More preferably, the yeast is selected from the group of *Pichia kiuveri, Sacchraromyces cerevisiae, Saccharomyces italicus* and *Kluyveromyces lactis*.

Condition of Fermentation:

The fermentation in step ii) is performed at a suitable temperature. The temperature should be so as to ensure activity of the microorganisms used, i.e. it should not be below 5° C. or above 55° C. Hence, the temperature during the fermentation is in the range of 5° C. to 55° C., preferably 8° C. to 50° C. In one embodiment, the temperature may be in the range of 10° C. to 45° C. In another embodiment, the temperature is from 10° C. to 40° C.

The fermentation can be performed at different temperature ranges. For example, the fermentation can be performed at 10° C. to 35° C., preferably from 15° C. to 32° C., even more preferably 20° C. to 32° C. In one embodiment of the present invention, the feed material inoculated with microorganisms is fermented in step ii) at an average temperature in the range of 8° C. to 50° C., such as between 15° C. to 40° C. In another embodiment of the invention, the fermentation is performed at a temperature between 10° to 39° C., 15° C. to 37° C., 18° C. to 35° C., 20° C. to 33° C., 22° C. to 32° C. or around room temperature. In yet another embodiment, means for monitoring and controlling the temperature are provided. The fermentation temperature may be constant or it may vary.

The fermentation may also be performed at a pH optimal for fermentation. The suitable pH may be dependent on the microorganisms used for fermentation.

In an embodiment of the invention, the pH during fermentation in step ii) is in the range from 3.5 to 8.5, such as from 4.0 to 7.5, preferably from 5.0 to 6.0, even more preferably a pH in the range of from 5.3 to 5.7.

During fermentation, the pH may be decreased due to convertion of lactic acid. However, in preferred embodiments of the invention the pH is controlled by adding a basic solution such that pH is maintained at a range from 3.5 to 8.5.

The time to reach near-zero growth and to start harvesting the flavoured liquid depends mainly on the preferred growth rate and lasts from approximately 2 to 5 days. However, by using a higher dilution rate in the first few hours this time can be shortened to less than 1 day. The dilution rate that can be used in these hours is lower but close to the maximum growth rate of the used microorganism in the order of 1 $h^{-1}$.

Flavour Development:

The amino acids and small peptides in the feed material are converted to flavour components during the fermentation. The flavour development is depending on the type of hydrolysed proteins and/or the composition of free amino acids present in the feed material, and the type of microorganisms used during the fermentation. For example, fermentation of amino acids and/or small peptides from milk proteins with lactic acid bacteria leads to a flavour resembling cheese. Peptides and amino acids from other proteins and the use of other microorganisms may lead to other flavours.

Amino acids are first converted to alpha-keto acids, and the alpha-keto acids can be further converted to flavour components such as aldehydes, ketones, acids, alcohols, and sulphuric components dependent on the amino acids.

Liquid Flavouring Ingredient:

An aspect of the invention relates to a liquid flavouring ingredient obtainable by the process according to the invention. The flavour and aroma of the liquid flavouring ingredient may vary and is dependent on the type of hydrolysed protein used in the fermentation and the composition of peptides and free amino acids in the feed material.

Use of the Liquid Flavouring Ingredient:

A further aspect of the invention relates to the use of the liquid flavouring ingredient according to the present invention in a food product.

The food product may be any food product, where a flavouring liquid could be added. In an example, the food product may be selected from the group consisting of dairy products, sauces, dressings, seasonings, meat products, bread products, and sauerkraut.

In a preferred embodiment, the liquid flavouring ingredient is used in dairy products, such as cheeses, cheese analogues, and milk products. The liquid flavouring ingredient may also be used as a taste enhancer.

Another aspect of the invention relates to the use of a liquid flavouring ingredient according to the present invention as a taste enhancer.

The liquid flavouring ingredient obtainable by the process according to the present invention can be used as an ingredient in the cooking of food products and can therefore be added as a flavouring component, seasoning or taste enhancer in connection with cooking of any food.

It should be noted that embodiments and features described in the context of one of the aspects of the present invention also apply to the other aspects of the invention.

The invention will now be described in further details in the following non-limiting examples.

EXAMPLES

Example 1—Chemically Defined Feed Material

A chemically defined feed material for use in the process of the present invention is prepared by mixing of the following ingredients and add water:

5 g/kg lactose
10 g/kg Bacto™ Tryptone (trypsin digest of casein)
0-2.43 g/kg $(NH_4)_3$ citrate
2.67 g/kg $KH_2PO_4$
1.66 g/kg Na.acetate.$3H_2O$
10 g/kg 100× metal stock
10 g/kg 100× nucleotide stock
10 g/kg 100× vitamin stock The Bacto™ Tryptone is a digest of casein having a content of hydrolysed protein being about 78.2% by weight, including 26.9% by weight free amino acids. Thus, the amount of hydrolysed protein in the chemical defined feed material is 0.78% by weight. The chemical defined feed material has a pH of 5.5.

The vitamin stock, the nucleotide stock and the metal stock have the following compositions:
The 100× Vitamin Stock:
0.2 g/kg pyridone-HCl
0.5 g/kg pyridoxamine-HCl
0.1 g/kg nicotinic acid
0.1 g/kg thiamine-HCl
0.1 g/kg Ca-(D+)-panthothenate
1 g/kg Na-p-aminobenzoate
0.25 g/kg D-biotin
0.1 g/kg Folic acid
0.5 g/kg vitamin B12
0.5 g/kg orotic acid
0.5 g/kg thymidine
0.5 g/kg inosine
0.25 g/kg DL-6,8-thioctic acid
100× Nucleotide Stock:
1 g/kg adenine
1 g/kg uracil
1 g/kg xanthine
1 g/kg guanine
100× Metal Stock:
20 g/kg $MgCl_2.6H_2O$
5 g/kg $CaCl_2.2H_2O$
0.5 g/kg $ZnSO_4.7H_2O$
0.25 g/kg $CoCl_2.6H_2O$
1.6 g/kg $MnCl_2.4H_2O$
0.25 g/kg $CuSO_4.5H_2O$
0.25 g/kg $(NH_4)_6Mo_7O24.4H_2O$
0.3 g/kg $FeCL_3.6H_2O$
0.5 g/kg $FeSO_4.7H_2O$ Example 2—Determination of Difference in Flavour Formation in Flavoured Liquid with Microorganisms and without Microorganisms An example was made where the flavour formation of a liquid flavoured ingredient prepared by the process according to the present invention was compared to a liquid flavour ingredient where all microorganisms were removed prior to the analysis.

A chemical defined feed material as in example 1 was used and the fermentation process according to the present invention was performed by fermenting with *Lactococcus lactis* subspecies *lactis* biovar *diacetylactis* at pH 5.5 at 30° C. Flavoured liquid with microorganisms was removed from the bioreactor and a sample of flavoured liquid with microorganisms and a flavoured liquid without microorganisms was analysed by SPME and GC-MS for flavour and aroma formation. Microorganisms were separated from the flavoured liquid (fermentation permeate) by cross-flow microfiltration.

Figure 3:
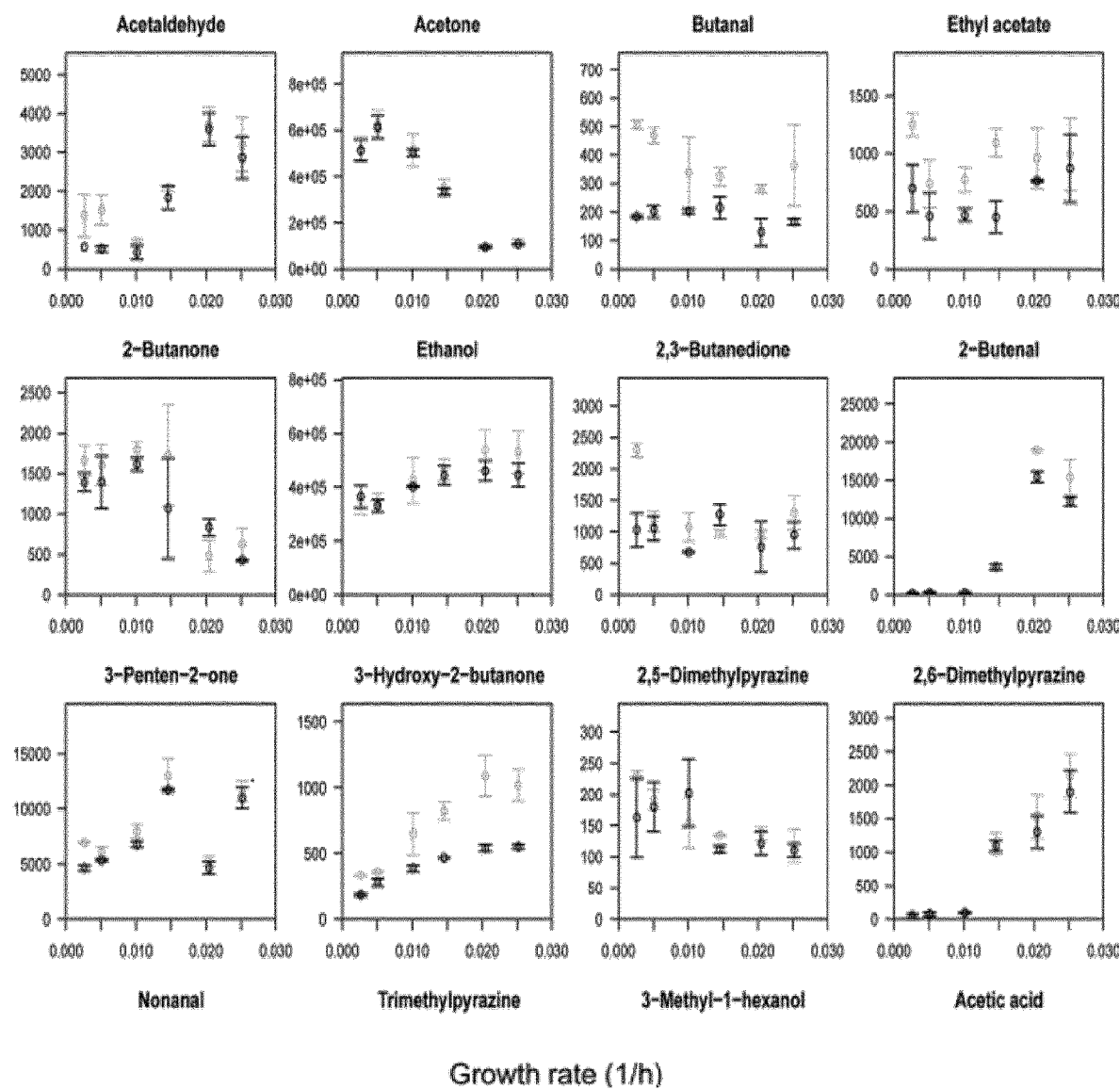
FIG. 3 shows the effect on aroma formation of fermented liquid with microorganisms versus fermented liquid with no microorganisms. The aroma formation is shown for different growth rates of the microorganisms in the fermentation process.
Figure 3:
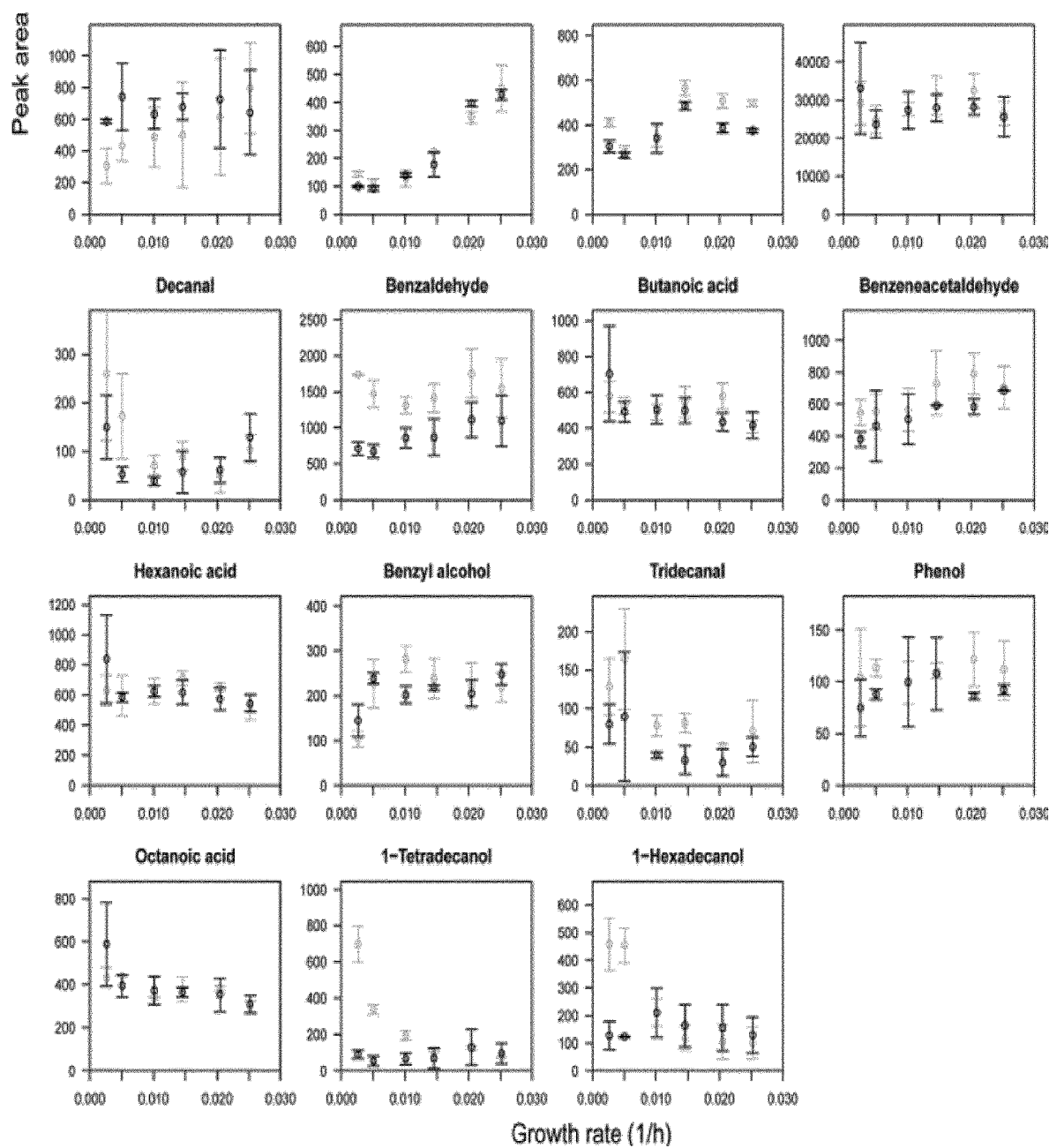

FIG. 3 shows the different patterns of flavour formation by showing the formation of different compounds by using SPME and GC-MS. The grey symbols represent samples with microorganisms present, and the black symbols represent samples with no microorganisms.

A difference is clearly shown, and some flavour compounds, mainly hydrophobic compounds, are present in higher amounts when microorganisms are present in the flavoured liquid as compared to when no microorganisms are present in the flavoured liquid. For example, flavoured liquid with microorganisms comprises a higher amount of the flavour compounds acetaldehyde, butanal, ethyl acetate, 3-hydroxy-2-butanone, benzaldehyde, 1-tetradecanol and 1-hexadecanol.

The biomass concentration in flavoured liquid depends on the concentration of nutrients in the feed material, the feed flow (dilution rate) and the growth rate. By choosing appropriate setting for the substrate concentration, flow rate and recycle ratio, the biomass concentration can be controlled, even at high concentrations in the bioreactor and high in the effluent (obtained flavoured liquid).

In FIG. 3 also the effect of the growth rate on the production of aroma compounds is shown. Particular compounds increased at higher growth rates (>0.015 $h^{-1}$), e.g. acetaldehyde, 2-butenal and 2,6-dimethylpyrazine, while other compounds clearly increased at lower growth rates, e.g. acetone, decanal, tridecanal, 1-tetradecanol, 1-hexadecanol. This shows that by making small changes in the growth rate, aroma production can be steered to an optimum dependent on the application.

Example 3—Determination of Optimal Recycling Ratio and Dilution Rate of Biomass

An example was made to show the optimal ratio of recycled biomass to the bioreactor when the chemical defined media was used as feed material.

A chemical defined feed material according to example 1 was used where the lactose content was 0.5% by weight, i.e. 5 g lactose per kg feed material. The Bacto-Tryptone content is 1%, and the growth rate was constant at 0.005 $h^{-1}$. The feed material was inoculated with *Lactococcus lactis* subspecies *lactis* biovar *diacetylactis* at pH 5.5 and 30° C.

Below in table 1, the dilution rate, recycle ratio and biomass content in the bioreactor are shown.

TABLE 1

| Dilution rate (feed flow rate/Volume) (1/h) | Recycle ratio | Biomass in bioreactor (gDW/kg) | Comment |
| --- | --- | --- | --- |
| 0.005 | 0 | 0.33 | Not desired because of low production rate and low biomass concentration |
| 0.01 | 0.5 | 0.67 | |
| 0.02 | 0.75 | 1.34 | |
| 0.03 | 0.833 | 2.01 | Less optimal but suitable |
| 0.04 | 0.875 | 2.68 | Optimal |
| 0.05 | 0.900 | 3.35 | Optimal |
| 0.075 | 0.933 | 5.02 | Optimal |
| 0.1 | 0.950 | 6.69 | Optimal |
| 0.2 | 0.975 | 13.39 | |
| 0.4 | 0.988 | 26.78 | |
| 1 | 0.995 | 66.95 | |
| 2 | 0.998 | 133.90 | Not desired because mixing will be difficult (Not homogeneously mixed) |

As seen from the above table 1, no recycling at all is not desired, since the production rate becomes low and the biomass concentration becomes low. Furthermore, it is not desired with a recycling ratio close to 1, since then mixing of the cell suspension in the bioreactor becomes difficult due to a high viscosity. The liquid in the bioreactor becomes viscous when having high biomass concentrations. Moreover, at high biomass concentration, the filter might clog quickly.

Biomass concentrations ranging between 2-10 g dw/kg are preferred. This biomass concentration is not only depending on the dilution rate and the recycle ratio (which is determined together with the growth rate) but also on the sugar concentration in the feed material.

Example 4—Determination of Optimal Ratio Between Sugar (Lactose) and Amino Acids An example was made to find the optimal ratio between sugar (lactose) and amino acids. A chemical defined feed material as in example 1 was used. The lactose content was kept constant at 0.5% by weight, but the amount of Bacto-Tryptone varied. Fermentation was performed with *Lactococcus lactis* subspecies *lactis* biovar *diacetylactis* at temperature 30° C. and pH 5.5. Flavour formation was observed. See table 2 below.

TABLE 2

| Lactose concentration (w/w %) | Amino acid concentration (w/w %) | Ratio lactose/amino acids | Comment |
| --- | --- | --- | --- |
| 0.5 | 0.05 | 10 | Not desired. Amino acids are limiting growth and no amino acids left for aroma formation. |
| 0.5 | 0.1 | 5 | |
| 0.5 | 0.25 | 2 | Less optimal, but suitable |
| 0.5 | 0.5 | 1 | optimal |
| 0.5 | 1 | 0.5 | optimal |
| 0.5 | 2.5 | 0.2 | good |
| 0.5 | 5 | 0.1 | Less optimal, but suitable |
| 0.5 | 10 | 0.05 | |

From table 2 it is shown that the ratio between lactose and amino acids preferably should be from 2:1 to 1:10.

This example was repeated, but with a constant amino acid concentration and varying lactose concentration. The result is shown in table 3 below.

TABLE 3

| Lactose concentration (w/w %) | Amino acid concentration (w/w %) | Ratio lactose/amino acids | Comment |
| --- | --- | --- | --- |
| 0.05 | 0.5 | 0.1 | |
| 0.1 | 0.5 | 0.2 | good |
| 0.25 | 0.5 | 0.5 | optimal |
| 0.5 | 0.5 | 1 | optimal |
| 1 | 0.5 | 2 | Less optimal, but suitable |
| 2.5 | 0.5 | 5 | |
| 5 | 0.5 | 10 | Not desired. Amino acids are limiting growth and no amino acids left for aroma formation. And growth inhibition by high organic acid concentrations (~500 mM) |

Table 3 confirms what is seen in table 2, i.e. that the ratio between lactose and amino acids preferably should be from 2:1 to 1:5.

Example 5—Determination of Optimal Sugar (Lactose) Concentration in the Bioreactor An example was made to find out the optimal lactose concentration in the feed material based on biomass concentration in the bioreactor. A chemical defined feed material as shown in example 1 was used. The growth rate of biomass was kept constant at 0.005 h$^{-1}$ and the dilution rate was kept constant at 0.05 h$^{-1}$. The ratio of lactose to hydrolysed protein (amino acids) was 1:2 and the temperature was kept at 30° C. and the pH at 5.5.

The lactose concentration and biomass concentration is shown in table 4 below.

TABLE 4

| Lactose concentration (w/w %) | Biomass (gDW/kg) | Comment |
| --- | --- | --- |
| 0.05 | 1.67 | Not desired because of low expected flavour concentration. |
| 0.1 | 3.35 | |
| 0.25 | 8.37 | Optimal |
| 0.5 | 16.7 | Optimal |
| 0.75 | 25.1 | Optimal |
| 1 | 33.5 | Optimal |
| 2 | 66.9 | |
| 3 | 100.4 | Not desired because of product inhibition (>300 mM organic acids) |
| 4 | 133.9 | |
| 5 | 167.4 | |

A lactose concentration between 0.25 and 1% w/w is preferred to obtain a relatively high biomass concentration (~10 gDW/kg) while preventing growth inhibition due to high lactic acid concentration.

Example 6—Determination of Preferred pH

An example was made to find out the optimal pH during fermentation and the influence of lactose limitation. A chemical defined feed material was used as shown in example 1. The growth rate of biomass during fermentation was kept constant at 0.13 h$^{-1}$ and the dilution rate was kept constant at 0.13 h$^{-1}$. The temperature was 30° C.

Samples were made where the pH during fermentation was 5.5 or 7.0 and the nutrient limitation was either lactose, i.e. the ratio of lactose to protein was 1:2 (0.5% lactose and 1% Bacto-tryptone), or the limitation was amino acids, i.e. the ratio of lactose to protein was 20:1 (2% lactose and 0.1% Bacto-tryptone).

Figure 4:
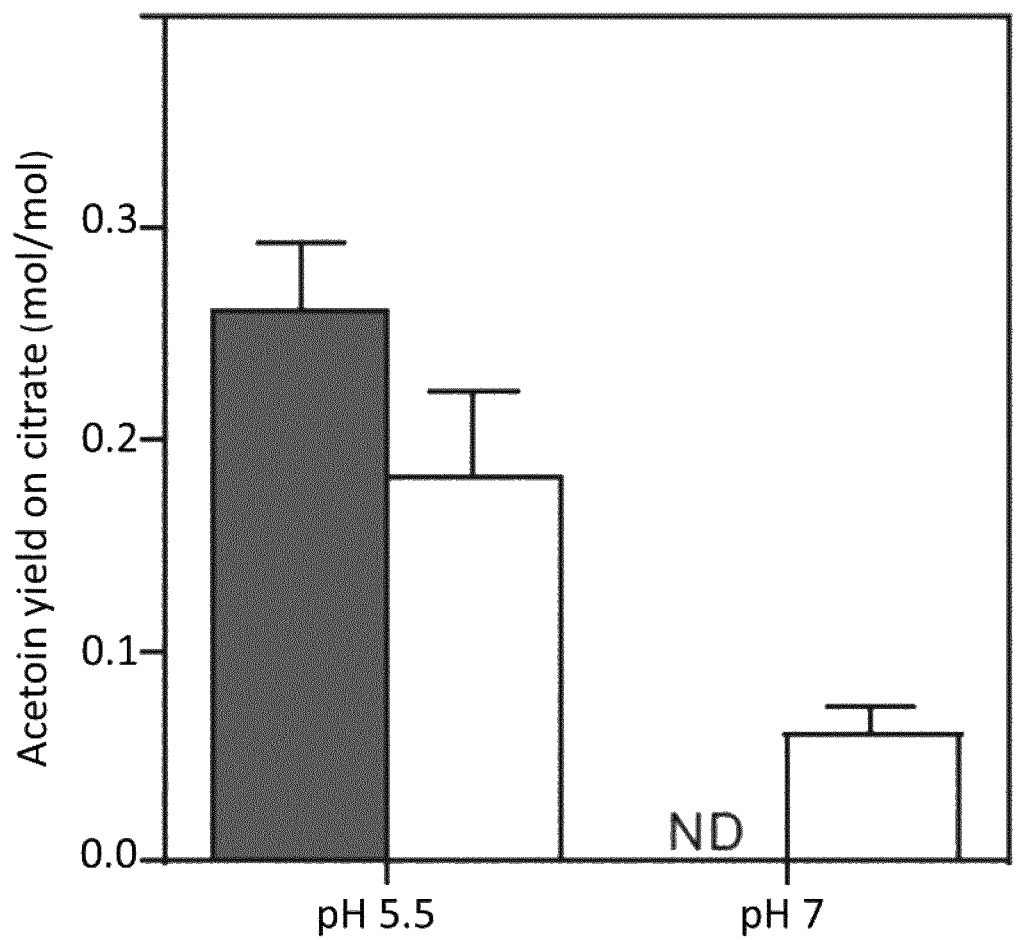
FIG. 4 shows the acetoin (aroma compound) content when fermentation was made with lactose limitation versus amino acid limitation. The figure also shows acetoin content when different pH was used during the fermentation process.

The aroma compound acetoin was measured for the three samples. FIG. 4 shows the amount of acetoin of the samples. The grey columns shows lactose limitation, where the white columns show amino acid limitation.

From FIG. 4, it is shown that Acetoin, which is a preferred aroma compound, has the highest abundance at pH 5.5 under lactose limitation (grey column). Especially the low pH (5.5) was observed to be important.

Example 8—Liquid Flavour Formation with Milk as Feed Material

An example of fermentation according to the present invention with milk as feed material was made.

Milk was microfiltrated by filtering through a microfiltration membrane having a pore size of 1.4 micrometer to remove whey protein and hence obtain a micellar casein isolate (MCI). The MCI was then neutralised to pH 8 with NaOH and was incubated 30 minutes with Alcalase at 50° C. to hydrolyse proteins. After the incubation, alcalase was inactivated by increasing the temperature to 85° C. for 15 minutes. After heat treatment, pH was adjusted to pH 7 with hydrochloric acid and neutrase was added for 4 hours at 50° C. for further hydrolysis. After hydrolysis with neutrase, neutrase was inactivated at 85° C. for 15 minutes. Then flavourzyme was added and hydrolysis was performed for 18 hours at 50° C., before inactivation of flavourzyme at 85° C. for 15 minutes.

The hydrolysed MCI was microfiltered with a 0.2 micrometer pore size microfilter with or without crossflow to remove impurities and to create the final substrate. Finally the hydrolysed and microfiltered MCI was heat treated at 140° C. for 4 seconds. Hereby a hydrolysed milk product in the form of hydrolysed micellar casein isolate (MCI) was made.

0.4% lactose monohydrate (Merck 1.077660) was added to the obtained hydrolysed MCI feed material to reach a lactose content of 0.5% by weight in the MCI feed material. 1 L of the hydrolysed MCI feed material was incubated with *Lactococcus lactis* subsp. *diacetylactis* and fermented at 25° C. for 16 days. Different feed materials was prepared and the flow hereof is shown in table 5.

TABLE 5

| Feed inlets | Feed$_{in}$ (F$_{in}$) | Feed rate |
|---|---|---|
| 6M NaOH (pH adjustment) | 0.00002 L/h | 0.00002 h$^{-1}$ |
| F$_{in\ max\text{-}with\ media\ added\ lactose}$ | 0.0059 L/h | 0.0059 h$^{-1}$ |
| F$_{in\ optimal\text{-}with\ media\ added\ lactose}$ | 0.0042 L/h | 0.0042 h$^{-1}$ |
| F$_{in\ min\text{-}with\ media\ not\ added\ lactose}$ | 0.0042 L/h | 0.0042 h$^{-1}$ |

NaOH was continuously added for pH adjustment to a pH of approximately 5.5. F$_{in\ max\text{—with\ media\ added\ lactose}}$, which refers to hydrolysed MCI with lactose added, was used to start the fermentation and quickly obtain a high amount of microorganisms. When the zero growth condition was obtained, a media of hydrolysed MCI without lactose added was used for the fermentation, i.e. "F$_{in\ optimal\text{—with\ media\ not\ added\ lactose}}$" and "F$_{in\ min\text{—with\ media\ not\ added\ lactose}}$". Samples were taken before fermentation and of the fermented liquid. The samples were analysed after day 1, 2, 6, 7, 8, 9, 12, 13, 14, 15 and 16 for the following: volatile compounds, microbial content, and sensory evaluation. The data is shown in table 6 below.

Aroma profile of the permeate after day 6, day 8, day 12, day 16 and the retentate at day 12 was analysed by GC-MS. The permeate is the flavoured liquid removed from the bioreactor, while the retentate is what is maintained in the bioreactor. The result is shown in the below table 7.

TABLE 7

|  | Reference, Hydrolysed MCI media | Permeate day 6 | Permeate day 8 | Permeate day 12 | Permeate day 16 | Retentate day 12 |
|---|---|---|---|---|---|---|
| Butanal, 2-methyl- | 0.0073 | 0.0018 | 0.0018 | 0.0020 | 0.0024 | 0.0027 |
| Butanal, 3-methyl- | 0.0260 | 0.0080 | 0.0073 | 0.0070 | 0.0067 | 0.0053 |
| Benzaldehyde | 0.0371 | 0.0056 | 0.0050 | 0.0075 | 0.0126 | 0.0056 |
| Propanoic acid, 2-methyl- | 0.0003 | 0.0003 | 0.0003 | 0.0024 | 0.0046 | 0.0018 |
| Butanoic, 3-methyl | 0.0003 | 0.0010 | 0.0010 | 0.0267 | 0.0496 | 0.0222 |

From table 7, a development of the compounds benzaldehyde, propanoic acid and butanoic acid in the permeate is shown over time.

In addition, a sensory evaluation was performed. 5 ml of fermented liquid was added to 100 gram of natural fresh cream cheese and evaluated sentorically at day 1, day 6 and day 16.-

TABLE 6

|  | pH | Cfu/ml | Removed By efflux | Removed permeate | Added media with 0.5% lactose | Added media with low lactose | PH after added media | Added 6M NaOH or 5M HCl | pH adjusted |
|---|---|---|---|---|---|---|---|---|---|
| Day 1 | 5.26 | 12 × 10$^8$ | 100 ml |  | 100 ml |  |  | 1.2 ml | 5.53 |
| Day 2 | 5.44 | 29 × 10$^8$ | 100 ml |  | 100 ml |  | 5.64 | 0.5 ml | 5.58 |
| Day 6 | 5.52 | 14 × 10$^8$ | 100 ml | 100 ml |  | 200 ml |  |  |  |
| Day 7 | 5.58 | 19 × 10$^8$ | 100 ml |  |  | 100 ml | 5.59 |  |  |
| Day 8 | 5.61 | 20 × 10$^8$ | 100 ml | 35 ml |  | 162 ml |  | 1.0 ml | 5.70 |
| Day 9 | 5.69 | 18 × 10$^8$ | 100 ml |  |  | 100 ml | 5.89 | 1.2 ml | 5.58 |
| Day 12 | 5.59 | 94 × 10$^8$ | 163 ml | 40 ml |  | 200 ml | 5.89 | 1.5 ml | 5.56 |
| Day 13 | 5.52 | 10 × 10$^8$ | 100 ml |  |  | 100 ml |  |  |  |
| Day 14 | 5.58 | 12 × 10$^8$ | 112 ml | 45 ml |  | 155 ml | 5.69 | 1.0 ml | 5.49 |
| Day 15 | 5.54 | 51 × 10$^8$ | 100 ml |  |  | 100 ml | 5.60 | 1.0 ml | 5.45 |
| Day 16 | 5.47 | 16 × 10$^8$ | 118 ml | 38 ml |  | 156 ml | 5.65 | 1.0 ml | 5.53 |

At day 1: the sensory attributes were evaluated as "substrate tasting"

At day 6: No change was observed

At day 12: The taste had changed and got the perception of being more sour, having more flavour and being slightly bitter. This is probably due to an increase in propanoic acid, benzaldehyde and butanoic acid and a slight decrease in butanal.

Example 9—Fermentation of Hydrolysed MCI According to the Invention and Analysis of Amino Acid Content and Flavour Development Another example of fermentation of a hydrolysed MCI was made.

Milk was microfiltrated, hydrolysed and heat treated as described in example 8 to prepare a hydrolysed MCI.

0.4% lactose monohydrate (Merck 1.077660) was added to the obtained hydrolysed MCI feed material to reach a lactose content of 0.5% by weight in the MCI feed material.

At day 0: 1 L of the hydrolysed MCI feed material with lactose added (media) was incubated with *Lactococcus lactis* subsp. *diacetylactis* and fermented without removing any fermentation liquid or microorganisms in order to upconcentrate the microorganisms.

At day 7: Dual efflux started such that liquid (also called effluent or permeate) with microorganisms was removed from the bioreactor and a part of the microorganisms was recycled to the bioreactor together with new media was added to the bioreactor. Hence, during dual efflux the flow of liquid through the fermentor was continuous.

At day 14: The zero growth rate condition started, meaning that the level of miroorganisms/bacteria was constant. At zero growth, the fermentation was still with dual-efflux. After zero growth condition started, the feed material used was hydrolysed MCI without lactose added.

From day 96, a chemically defined feed material (media) as described in example 1 was added to the fermentor instead of the media of hydrolysed MCI.

At the start of the fermentation, hydrolysed MCI added lactose was used as the feed material to quickly obtain a high amount of microorganisms in the bioreactor. When the zero growth condition began, the feed material used was hydrolysed MCI without lactose added. Hence, the lactose present is only from MCI, about 0.3 g lactose per 100 g hydrolysed MCI.

NaOH was continuously added for pH adjustment to approximately pH 5.5.

In table 8 is the feed flow shown of the different feed materials used.

TABLE 8

| Feed inlets | Feed$_{in}$ (F$_{in}$) | Feed rate |
|---|---|---|
| 6M NaOH (pH adjustment) | Set to automatically obtain a pH of 5.5 | |
| F$_{in\ optimal-with\ media\ added\ lactose}$ | 0.0198 L/h | 0.0198 h$^{-1}$ |
| F$_{in\ optimal-with\ media\ not\ added\ lactose}$ | 0.0030 L/h | 0.0030 h$^{-1}$ |

The volume in the bioreactor is constantly 1 L. Hence, when feed material is added to the bioreactor, the same amount is removed, i.e. to give a flux through the bioreactor.

The following samples from the fermention liquid (permeate) were collected for further analysis Day 0: Start of fermentation—hydrolysed MCI added lactose and *Lactococcus lactis*

Day 7: at beginning of Dual efflux

Day 14: before beginning of zero growth condition

Day 48: 34 days of fermentation under zero growth

Day 96: 82 days of fermentation under zero growth condition

Day 101: 87 days of fermentation—5 days after the chemical defined feed material was added Day 123: 109 days after fermentation—27 days after the chemical defined feed material was added Further, samples was collected of:

Hydrolysed MCI with lactose added to 0.5 g/100 g

Hydrolysed MCI with no lactose added, i.e natural lactose content of MCI (0.3 g/100 g)

The chemically defined feed material of example 1

A sample of the fermentation retentate (biofilm in the bioreactor) at day 123

Figure 5:
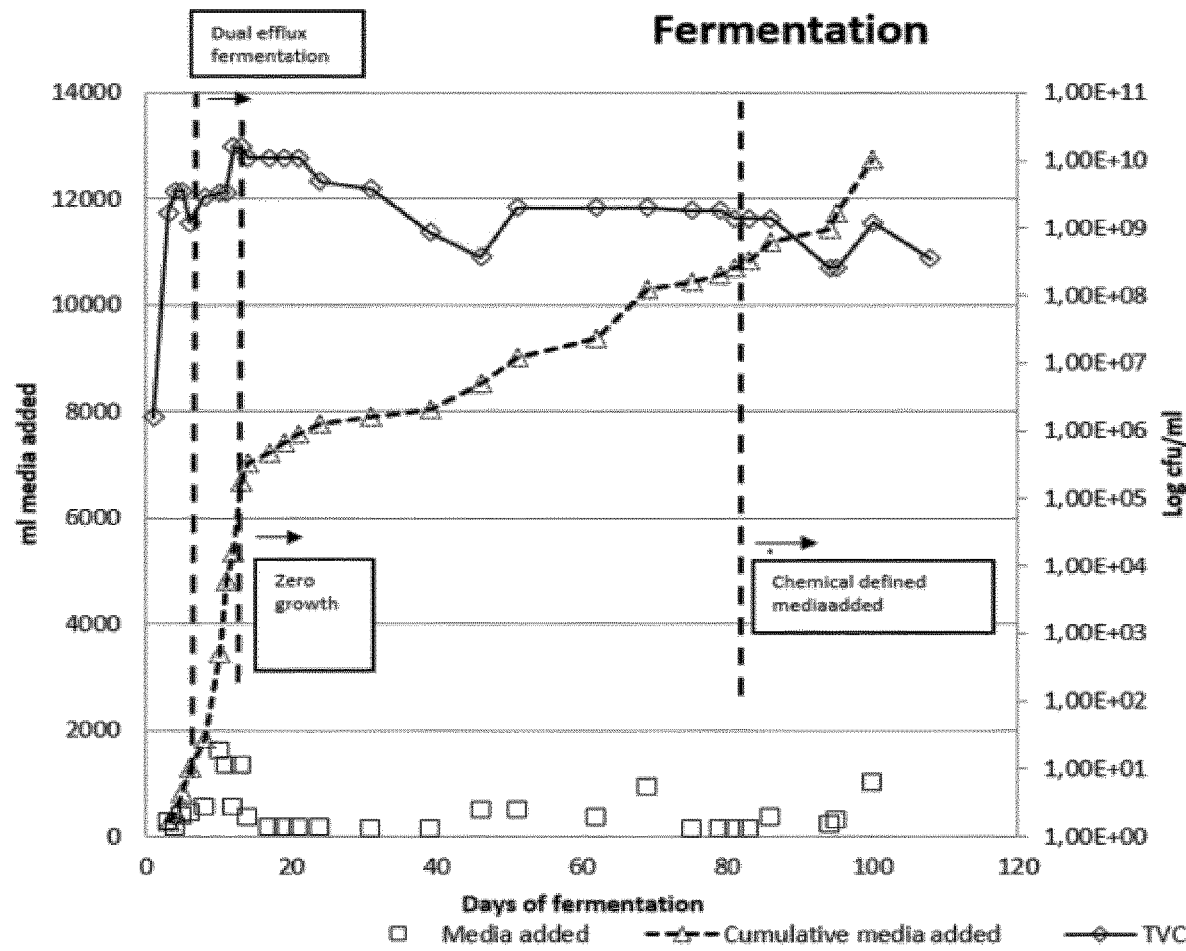
FIG. 5 shows a schematically overview of the fermentation experiment according to the invention and as set out in example 9. The start of dual efflux and the start of the zero growth condition are shown together with the time where the chemical defined media was added.

FIG. 5 shows a schematically overview of the fermentation experiment in example 9, including when dual efflux started, when the zero growth condition started and when the chemical defined media was added. The term "TVC" in FIG. 5 is an abbreviation of "total viable count", i.e. the total amount of microorganisms, e.g. bacteria present.

The samples collected was analysed for the content of free amino acid content by Eurofins using their method of determining the amino acid profile with Tryptophan, analysis No. PDJ02-1. The free amino acid content of the different samples are shown in table 9 below:

TABLE 8

| | Media, MCI + lactose (g/100 g media) | Media, MCI no lactose (g/100 g) | Sample after start of dual-efflux (up-concentrated) (g/100 g media) | Sample before zero-growth (Day 14) (g/100 g media) | Sample before adding chemical defined media (g/100 g media) | Chemical defined media (g/100 g media) | Sample after adding chemical defined media (g/100 g) | Sample at end of fermentation (g/100 g media) | Sample of biofilm from bioreactor (retentate) (g/100 g media) |
|---|---|---|---|---|---|---|---|---|---|
| Lysine | 0.527 | 0.527 | 0.482 | 0.495 | 0.539 | 0.0442 | 0.599 | 0.177 | 0.191 |
| Threonine | 0.291 | 0.291 | 0.250 | 0.256 | 0.298 | 0.0216 | 0.300 | 0.920 | 0.101 |
| Isoleucine | 0.309 | 0.309 | 0.287 | 0.285 | 0.321 | <0.035 | 0.359 | 0.105 | 0.116 |
| Leucine | 0.678 | 0.678 | 0.614 | 0.609 | 0.684 | 0.0476 | 0.755 | 0.207 | 0.217 |
| Histidine | 0.196 | 0.196 | 0.178 | 0.175 | 0.194 | <0.02 | 0.714 | 0.0591 | 0.0617 |
| Phenylalanine | 0.361 | 0.361 | 0.331 | 0.321 | 0.366 | <0.031 | 0.400 | 0.109 | 0.143 |
| Tyrosine | 0.363 | 0.363 | 0.325 | 0.311 | 0.301 | <0.023 | 0.308 | 0.0853 | 1.29 |
| Valine | 0.429 | 0.429 | 0.396 | 0.392 | 0.437 | 0.0370 | 0.485 | 0.143 | 0.152 |
| Alanine | 0.201 | 0.201 | 0.188 | 0.193 | 0.212 | 0.0186 | 0.232 | 0.0771 | 0.0894 |
| Arginine | 0.201 | 0.201 | 0.121 | 0.112 | 0.120 | 0.0220 | 0.125 | 0.0256 | 0.033 |

TABLE 8-continued

|  | Media, MCI + lactose (g/100 g media) | Media, MCI no lactose (g/100 g) | Sample after start of dual-efflux (up-concentrated (g/100 g media) | Sample before zero-growth (Day 14) (g/100 g media) | Sample before adding chemical defined media (g/100 g media) | Chemical defined media (g/100 g media) | Sample after adding chemical defined media (g/100 g media) | Sample at end of fermentation (g/100 g media) | Sample of biofilm from bioreactor (retentate) (g/100 g media) |
|---|---|---|---|---|---|---|---|---|---|
| Aspartic acid | 0.462 | 0.462 | 0.441 | 0.436 | 0.491 | 0.0386 | 0.232 | 0.163 | 0.183 |
| Glutamic acid | 1.44 | 1.44 | 1.39 | 1.31 | 1.46 | 0.113 | 1.70 | 0.477 | 0.470 |
| Glycine | 0.114 | 0.114 | 0.104 | 0.112 | 0.120 | <0.019 | 0.134 | 0.0441 | 0.0527 |
| Hydroxyproline | <0.05 | <0.05 | <0.05 | <0.05 | <0.05 | <0.05 | <0.05 | <0.05 | <0.05 |
| Ornitine | <0.05 | <0.05 | 0.0532 | 0.0643 | 0.0669 | <0.05 | 0.0742 | <0.05 | <0.05 |
| Proline | 0.728 | 0.728 | 0.691 | 0.655 | 0.724 | 0.0501 | 0.846 | 0.236 | 0.237 |
| Serine | 0.307 | 0.307 | 0.260 | 0.287 | 0.326 | 0.0237 | 0.316 | 0.110 | 0.115 |
| Cysteine + Cystine | 0.0210 | 0.0210 | 0.0170 | 0.0220 | 0.0200 | <0.006 | 0.0200 | 0.0077 | 0.008 |
| Methionine | 0.189 | 0.189 | 0.164 | 0.167 | 0.193 | <0.024 | 0.193 | 0.0539 | 0.059 |
| Tryptophan | 0.0787 | 0.0787 | 0.0668 | 0.0698 | 0.0714 | <0.01 | 0.0716 | 0.020 | 0.0235 |
| Lactic acid | 0.084 | 0.084 | 0.298 | 0.288 | — | 0.176 | 0.178 | 0.236 | 0.226 |
| Lactose | 0.690 | 0.690 | 0.238 | 0.210 | — | 0.151 | 0.154 | 0.0602 | 0.0587 |

From table 9, it is shown that the content of the different free amino acids are approximately the same during the fermentation, i.e. from the beginning of the fermentation until the chemical defined media is added. However, when the chemical defined media was added, the content of most of the free amino acids was decreased. Immediately after the chemical media was added, the content of the amino acids was not decreased, but at the end of the fermentation, i.e. 27 days after the chemical defined media was added, the content of diffent individual amino acids in the fermentation liquid (permeate) was decreased a lot. However, as seen from table 9, the content of free amino acids in the biofilm from the bioreactor (fermentation retentate) was also decreased. Thus, it can be concluded that the addition of the chemical defined media increases the fermentation of the free amino acids.

Without being bound by any theory, the inventors of the present invention believes that the increase in fermentation when adding the chemical defined madia may be because of either the higher amount of lactose present in the chemical defined media (0.5%—as compared to 0.3% in MCI) or the presence of nucleotides, vitamins and/or metals.

However, it is also shown in table 9 that the content of the amino acid Arginine is decreased already from dual-efflux and at zero-growth condition and during the fermentation until before the chemical defined media is added. After the chemical added media is added, the content of Arginine is however even further decreased.

Further, table 9 shows that the lactose content is decreased as compared to the media (hydrolysed MCI with and without lactose) used during the fermentation. Both the sample from beginning of dual-efflux and at zero growth condition has a lactose content much lower than the media used. This is an indication of lactose is used for the growth of microorganisms. However, it is also shown from table 9 that when the chemical defined media was added, the content of lactose at the end of the fermentation was very low both in the permeate and the retentate (biofilm of reactor)

The samples collected was also analysed for fatty acids, flavors, and aroma components by use of Gas Chromatography-Mass Spectrometry (GC-MS) and Solid Phase Micro Extraction (SPME). GC-MS is an analytical method that combines the features of gas-chromatography and mass spectrometry to identify different substances within a test sample. SPME is a solid phase extraction sampling technique that involves the use of a fiber coated with an extracting phase, that can be a liquid (polymer) or a solid (sorbent).

For the present analysis was an apparatus composed of different modules used. The apparatus included:
Gerstel Multi Prupose Sampler (MPS) for measuring analytics with SPME
Agilent (GC) Gaschromotography 7890B for measuring analytics with GC
Agilent (MSD) Mass Spectrometry 5977B HES for measureing analytics with MS
Agilent GC Column, HP-FFAP 19091F-433. 30.0 m ID: 0.25 mm, Film: 0.25 µm for measuring analytics with GC 5.0 ml of the samples were transferred to a 20 ml vial and analysed using SPME and GC-MS. Identification of the milk fatty acids, flavors and aroma components was done by comparing the samples to known fatty acid, flavor and aroma components in a dairy product.

The conditions of the SPME and GC-MS used is as disclosed in table 10:

TABLE 10

| SPME metal fiber | 65 µm polydimethylsiloxane/divinylbenzene |
|---|---|
| Incubation temperature | 50° C. |
| Incubation time | 10 min. |
| Extraction time | 40 min. |
| Desorption Time | 120 sec. |
| Inlet temperature | 250° C. |
| Inlet split | 5:1 |
| GC carrier gas | Helium |
| GC flow | 1.00 ml/min |
| GC column temperature | 40° C. in 2 min. Rate 5° C. to 200° C. in 12 min. |
| MS settings | Atune.u SSCAN, mw 30.0 to 500.0 |

The components analysed with SPME and GC-MS was acetoin; 1-Butanol; 1-Butanol, 3-methyl-; 2-furanmethanol; and phenylethyl alcohol.

Figure 6:
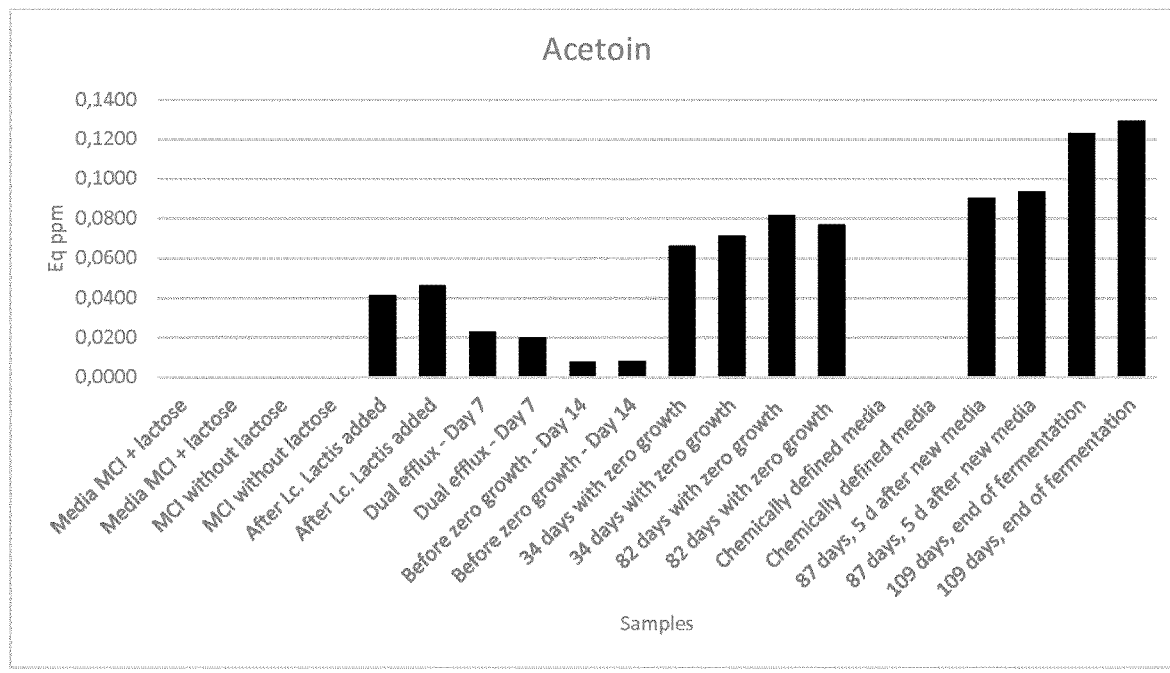
FIG. 6 shows the acetoin content of different samples of fermentation liquid from a fermentation according to the invention of hydrolysed micellar casein isolate.

In FIG. 6 is the content of acetoin measured in the samples shown. Acetoin is a compound that is present in cheese and therefore known as a cheese flavor compound. Acetoin contributes with a butterly flavor and aroma and acetoin is, along with diacetyl, one of the compounds giving butter its characteristic flavor and aroma. Thus, the presence of acetoin gives an indication of whether cheese flavor is developed. From FIG. 6, it is shown that the acetoin level is increasing during the fermentation after the zero growth condition. There is no acetoin in either the hydrolysed MCI with and without lactose media or the chemically defined media and therefore the acetoin content is not from the media. Furthermore, FIG. 6 shows that after addition of the chemically defined media, the amount of acetoin is further increased. Hence, also from SPME and GC-MS, it seems like the chemically defined media will speed up the fermentation and hence the convertion of amino acids into flavor compounds. However, also without addition of the chemical defined media a flavour development was observed.

Figure 7:
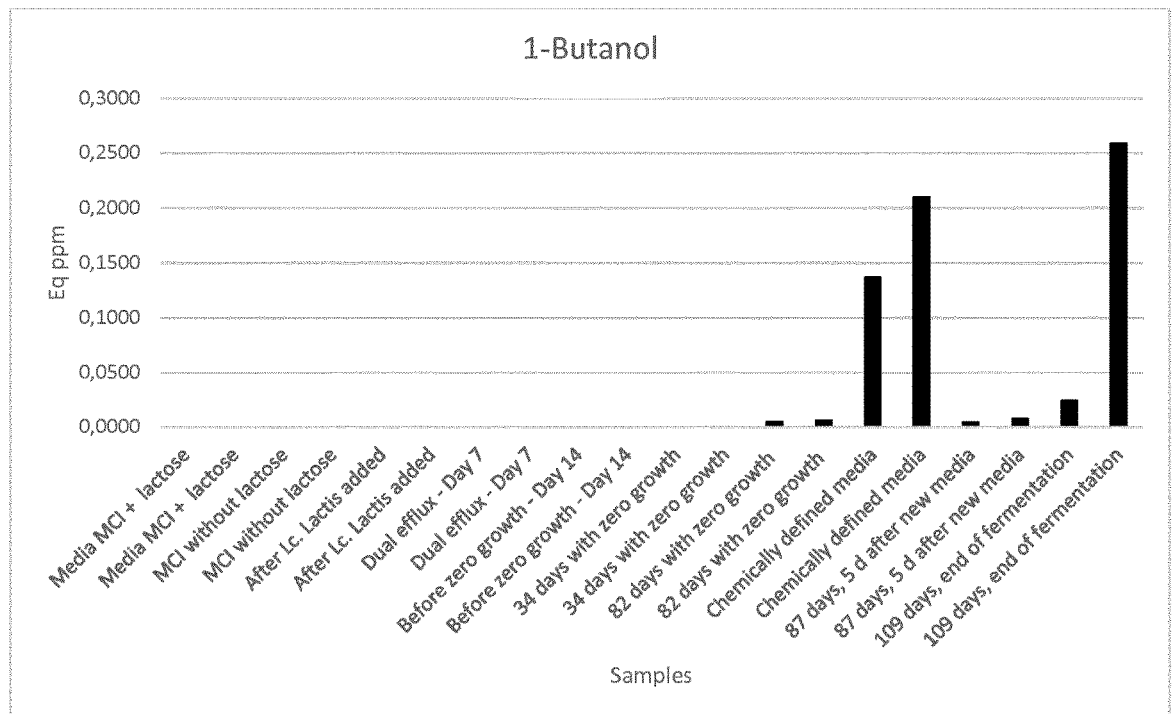
FIG. 7 shows the content of 1-Butanol of different samples of fermentation liquid from a fermentation according to the invention of hydrolysed micellar casein isolate.

In FIG. 7 is the content of 1-Butanol measured in the samples shown. 1-Butanol is also a flavorant found in for example cheese and butter. In FIG. 7, it is shown that the content of 1-Butanol is low for all samples exept the chemically defined media and the samples after end of the fermentation, where the level is high in both the sample of the permeate and the retentate (biofilm in the bioreactor). Further, it is observed from FIG. 7 that even though the chemically defined media comprises a certain level of 1-Butanol, the sample 5 days after adding the chemically defined media showed no content of 1-Butanol. Hence, that the amount of 1-Butanol is high at the end of the fermentation is an indication of 1-Butanol being developed during the fermentation after the chemically defined media is added. Furthermore, 1-Butanol being present in the biofilm is an indication of 1-Butanol being attached to the microorganisms (biofilm). Thus, 1-Butanol both being present in the fermentation permeate and the retentate is an indication of a liquid flavoring ingredient with some microorganisms present will obtain increased flavor development at least in the form of 1-Butanol.

Figure 8:
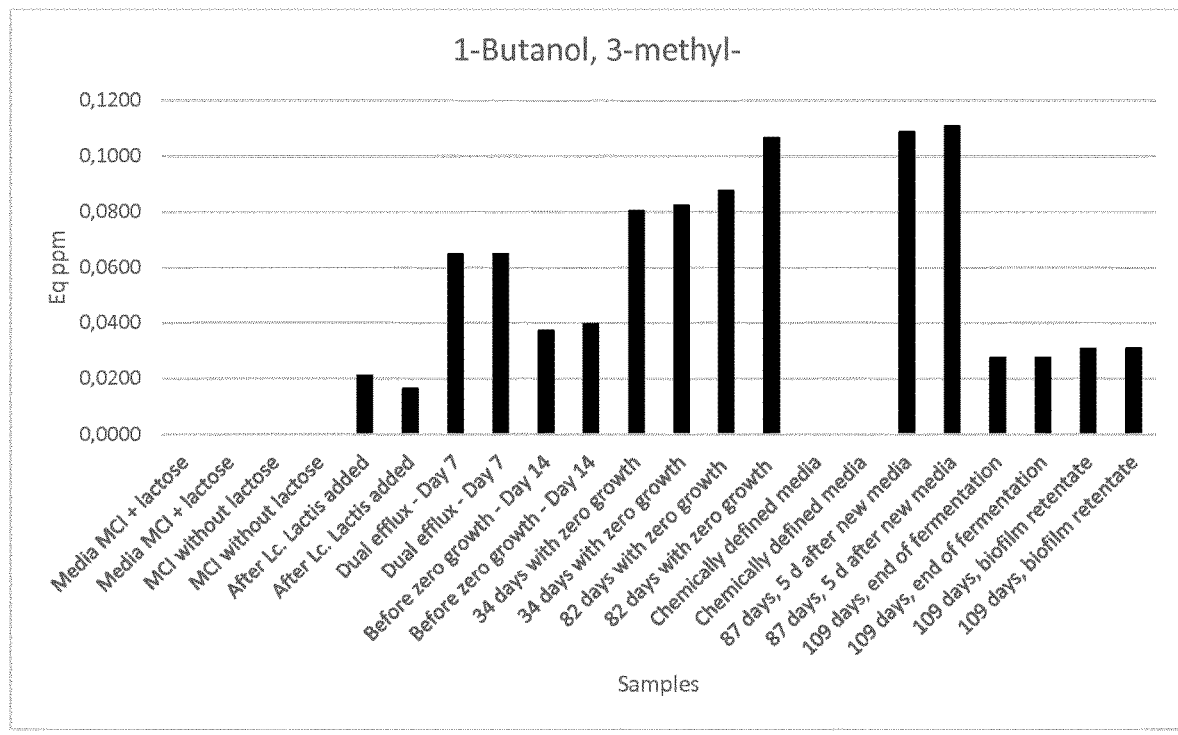
FIG. 8 shows the content of 1-Butanol, 3-methyl- of different samples of fermentation liquid from a fermentation according to the invention of hydrolysed micellar casein isolate.

FIG. 8 shows the content of 1-Butanol, 3-methyl-, and it is shown that neither the media with hydrolysed MCI or the chemically defined media comprises 1-Butanol, 3-methyl-. However, the fermentation liquid comprises increased amounts of 1-Butanol, 3-methyl-after fermentation under zero growth condition. FIG. 8 shows that the content of 1-Butanol, 3-methyl- is low at the end of the fermentation both in the fermentation liquid (permeate) and the biofilm (retentate). Without being bound by any theory, the inventors of the present invention believes that 1-Butanol, 3-methyl-after a certain time of fermentation will be converted to other components, properly other flavor components. 1-Butanol, 3-methyl-contributes to a nutty flavor.

Figure 9:
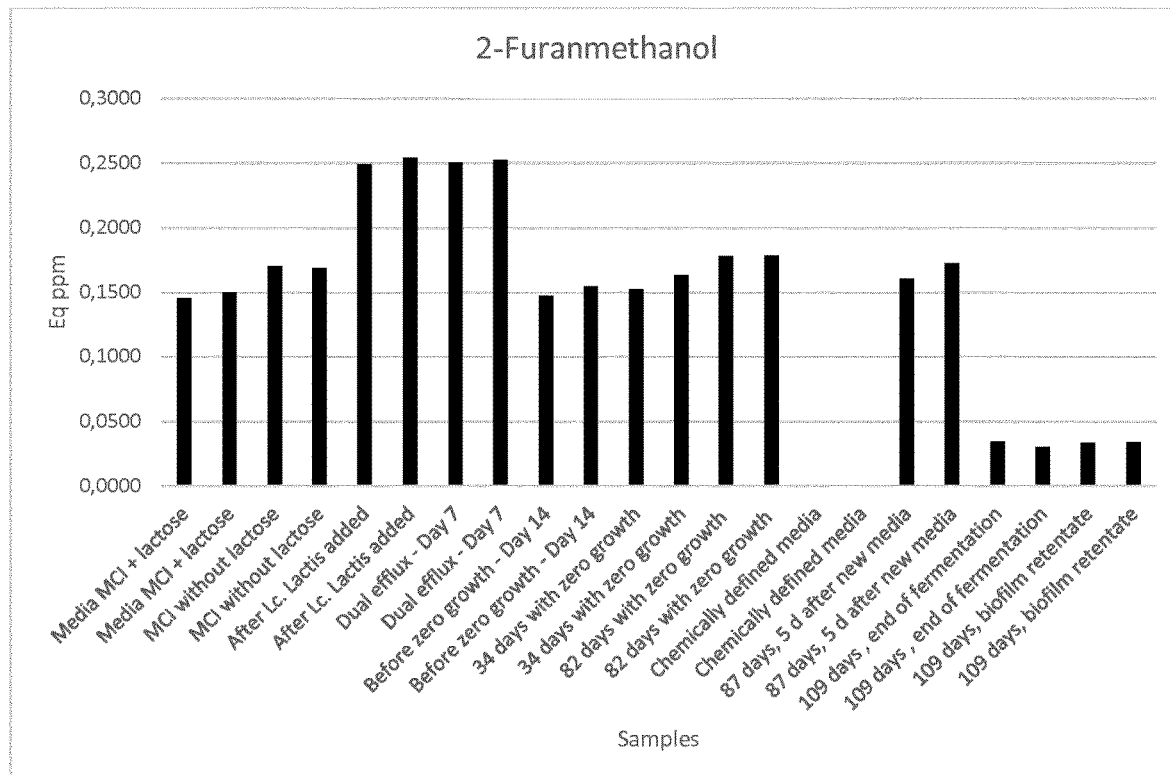
FIG. 9 shows the content of 2-Furanmethanol of different samples of fermentation liquid from a fermentation according to the invention of hydrolysed micellar casein isolate.

FIG. 9 shows the content of 2-Furanmethanol in the samples. 2-Furanmethanol is a maillard reaction product. 2-Furanmethanol is present in the media with hydrolysed MCI and lactose, which properly is because 2-Furanmethanol is formed during the hydrolysis process. However, at the end of the fermentation the content of 2-Furanmethanol is significantly decreased. This might be because 2-Furanmethanol is converted to other compounds.

Figure 10:
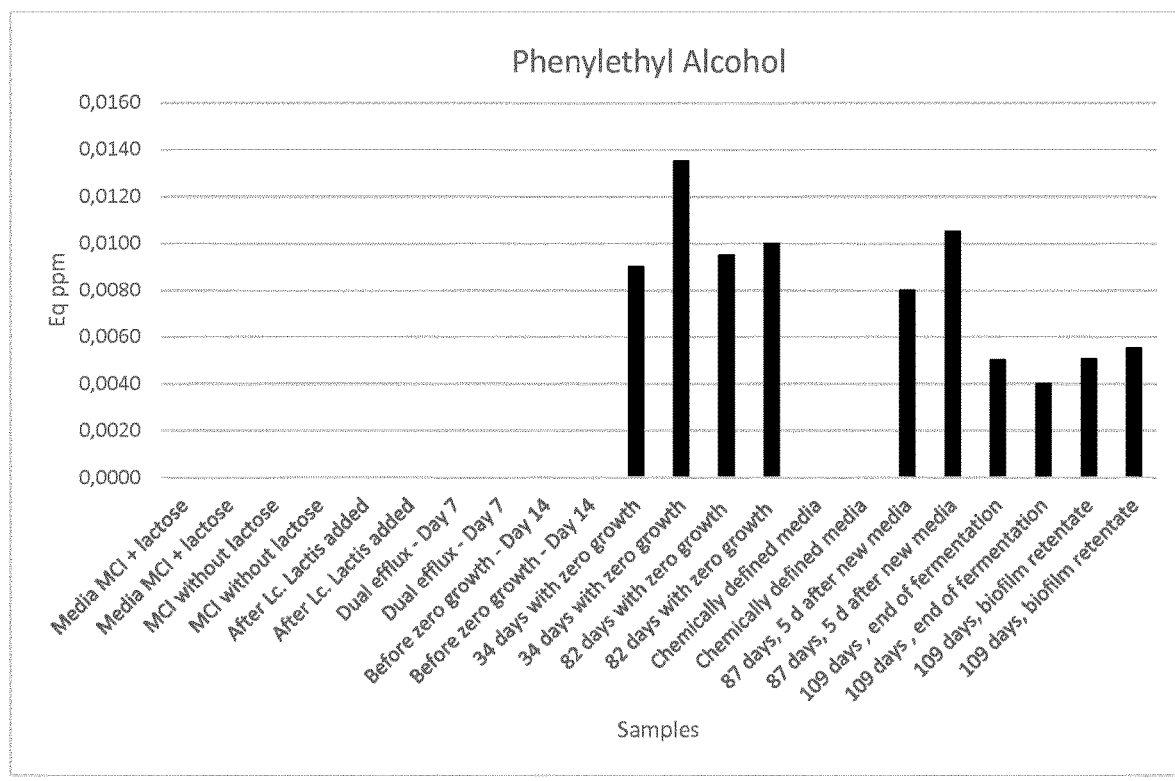
FIG. 10 shows the content of Phenylethyl Alcohol of different samples of fermentation liquid from a fermentation according to the invention of hydrolysed micellar casein isolate.

FIG. 10 shows the content of phenylethyl alcohol in the samples. Phenylethyl alcohol is known to contribute with a floral or rose like flavor. Phenylethyl alcohol is not present in either the media with hydrolysed MCI and lactose or the chemically defined media. However, phenylethyl alcohol is measured after 34 days with zero growth condition until the end of the fermentation, both in the fermentation liquid and the biofilm.

The invention claimed is:

1. A process for preparing a liquid flavouring ingredient, comprising:
    i) providing a feed material to be fermented, wherein said feed material comprises hydrolysed proteins and/or a mixture of free amino acids in a liquid solution in an amount of at least 0.1% w/v, and wherein the feed material comprises a) hydrolysed protein and/or free amino acids and b) one or more sugars, where the ratio of a) and b) is in the range of 1:2 to 15:1 by weight;
    ii) providing one or more microorganisms and inoculate the feed material of i) with the one or more microorganisms in a bioreactor and fermenting under conditions for growth to prepare a flavoured liquid with microorganisms, wherein the growth rate of the microorganisms is in the range of 0.001 to 0.1 $h^{-1}$;
    iii) removing flavoured liquid with microorganisms from the bioreactor; and
    iv) recycle a part of the microorganisms removed from the bioreactor in iii) back to the bioreactor, wherein 20-95% by weight of the microorganisms are recycled to the bioreactor; and maintain a part of the microorganisms removed from the bioreactor in iii) in the flavoured liquid to obtain a liquid flavouring ingredient.

2. The process according to claim 1, wherein the hydrolysed proteins and/or mixture of free amino acids is of dairy origin.

3. The process according to claim 1, wherein the feed material further comprises one or more sugars.

4. The process according to claim 1, wherein the feed material comprises hydrolysed proteins and/or free amino acids in the range of 0.1 to 15% w/v.

5. The process according to claim 1, wherein the process has a dilution rate in the bioreactor in the range of from 0.001 to 0.5 $h^{-1}$.

6. The process according to claim 1, wherein the concentration of microorganisms in the bioreactor is maintained in the range of $10^9$ to $10^{10}$ cells/ml.

7. The process according to claim 1, wherein the removing flavoured liquid with microorganisms from the bioreactor according to iii) is performed by removing the flavoured liquid with microorganisms from the one or more outlets present on the bioreactor.

8. The process according to claim 7, wherein after removing the flavoured liquid with microorganisms from the bioreactor, the microorganisms are separated from the flavoured liquid and a part of the separated microorganisms are recycled to the bioreactor and another part of the separated microorganisms are added to the flavoured liquid to obtain the liquid flavouring ingredient.

9. The process according to claim 7, wherein the removing of flavoured liquid with microorganisms from the bioreactor is performed by removing the flavoured liquid with microorganisms from two outlets present on the bioreactor, wherein:
    a) one outlet is used for removal of a first flavoured liquid with microorganisms followed by separation of the microorganisms from said first flavoured liquid, and wherein and said microorganisms are recycled to the bioreactor; and
    b) a second outlet is used for removal of a second flavoured liquid with microorganisms, and wherein
    c) said first flavoured liquid after removal of the microorganisms and said second flavoured liquid with microorganisms are mixed to obtain the liquid flavouring ingredient.

10. The process according to claim 1, wherein said microorganisms are separated from the flavored liquid by filtration, sedimentation and/or centrifugation.

11. The process according to claim 1, wherein the feed material further comprises one or more intact proteins, polysaccharides, fats, fatty acids, organic acids, or alcohols.

12. The process according to claim 1, wherein the microorganisms are one or more lactic acid bacteria, acetic acid bacteria, bifidobacteria or propionibacteria.

* * * * *